(12) United States Patent
Salter et al.

(10) Patent No.: US 7,132,249 B1
(45) Date of Patent: Nov. 7, 2006

(54) METHOD OF DETERMINING ALLERGENIC FOOD ON SURFACES

(75) Inventors: Robert S. Salter, Reading, MA (US); Stanley E. Charm, Boston, MA (US); Cheryl B. Francisco, Assonet, MA (US); Robert J. Markovsky, Brentwood, NH (US); Steven J. Saul, Arlington, MA (US)

(73) Assignee: Charm Sciences, Inc., Lawrence, MA (US)

( * ) Notice: Subject to any disclaimer, the term of this patent is extended or adjusted under 35 U.S.C. 154(b) by 0 days.

(21) Appl. No.: 10/843,495

(22) Filed: May 11, 2004

Related U.S. Application Data

(60) Provisional application No. 60/530,846, filed on Dec. 17, 2003, provisional application No. 60/507,058, filed on Sep. 29, 2003, provisional application No. 60/497,422, filed on Aug. 22, 2003, provisional application No. 60/469,707, filed on May 12, 2003.

(51) Int. Cl.
*C12Q 1/66* (2006.01)

(52) U.S. Cl. ........................................................ 435/8

(58) Field of Classification Search .................... 435/8, 435/288.7
See application file for complete search history.

(56) References Cited

U.S. PATENT DOCUMENTS

| | | | |
|---|---|---|---|
| 3,713,780 A | 1/1973 | Shapiro | |
| 3,745,090 A | 7/1973 | Chapelle et al. | |
| 3,871,767 A | 3/1975 | Holm-Hansen et al. | |
| 3,971,703 A | 7/1976 | Picciolo et al. | |
| 4,099,920 A | 7/1978 | Heiss | |
| 4,150,950 A | 4/1979 | Takeguchi et al. | |
| 4,303,752 A | 12/1981 | Kolehmainen et al. | |
| 4,312,950 A | 1/1982 | Snyder et al. | |
| 4,353,868 A | 10/1982 | Josline et al. | |
| 4,409,988 A | 10/1983 | Greenspan | |
| 4,707,450 A | 11/1987 | Nason | |
| 4,770,853 A | 9/1988 | Bernstein | |
| 4,806,415 A | 2/1989 | Fossati | |
| 5,004,684 A | 4/1991 | Simpson et al. | |
| 5,094,939 A | 3/1992 | Okada et al. | |
| 5,223,402 A | 6/1993 | Abbas et al. | |
| 5,238,649 A | 8/1993 | Nason | |
| 5,266,266 A | 11/1993 | Nason | |
| 5,283,179 A | 2/1994 | Wood | |
| 5,366,867 A | 11/1994 | Kawakami et al. | |
| 5,374,535 A | 12/1994 | Zomer et al. | |
| 5,618,682 A | 4/1997 | Scheirer | |
| 5,700,645 A | 12/1997 | Pahuski et al. | |
| 5,736,351 A | 4/1998 | Miller et al. | |
| 5,814,471 A * | 9/1998 | Wood ............................ | 435/8 |
| 5,827,675 A | 10/1998 | Skiffington et al. | |
| 5,905,029 A | 5/1999 | Andreotti et al. | |
| 5,908,751 A | 6/1999 | Higo et al. | |
| 5,916,802 A | 6/1999 | Andreotti | |
| 5,965,453 A | 10/1999 | Skiffington et al. | |
| 6,055,050 A * | 4/2000 | Skiffington ................. | 356/244 |
| 6,180,395 B1 * | 1/2001 | Skiffington et al. ...... | 435/287.6 |
| 6,503,723 B1 | 1/2003 | van Lune et al. | |
| 6,660,489 B1 | 12/2003 | Schrecengost et al. | |
| 6,716,595 B1 * | 4/2004 | Skinner et al. ................ | 435/8 |
| 2003/0104507 A1 | 6/2003 | Wood et al. | |
| 2004/0028608 A1 * | 2/2004 | Saul et al. .................... | 424/9.1 |

FOREIGN PATENT DOCUMENTS

| | | |
|---|---|---|
| EP | 0155747 A1 | 9/1985 |
| EP | 0309429 A2 | 3/1989 |
| EP | 1041151 A1 | 10/2000 |
| JP | 7-59555 | 3/1995 |
| WO | WO-90/04547 | 5/1990 |
| WO | WO-92/20781 | 11/1992 |
| WO | WO-95/07457 | 3/1995 |
| WO | WO-95/25948 | 9/1995 |
| WO | WO-96/14570 | 5/1996 |
| WO | WO-97/23596 | 7/1997 |
| WO | WO-02/066671 A2 | 8/2002 |

OTHER PUBLICATIONS

Valazquez M. et al. Quneching and Enhancement Effects of ATP Extractants, Cleansers, and Sanitizers on the Detection of the ATP Bioluminescence Signal. J. of Food Protection 60(7)799-803, 1997.*

Hattori N. et al. Mutant Liciferase Enzymes from Fireflies with Increased Resistance to Benzalkonium Chloride. Bioscience Biotechnology Biochemistry 66(12)2587-2593, 2002.*

Geerling G. et al. toxicity of Natural Tear Substitutes in a Fully Defined Culture Model of Human Corneal Epithelial Cells. Investigative Ophthalmology & Visual Science 42(5)948-956, Apr. 2001.*

Mecozzi M. et al. Computer Assisted Determination of ATP in Environmental and Food Samples by Bioluminescent Assay: Comparison of Algorithms. Computer Methods and Programs in Biomedicine 62(1)35-43, May 2000.*

Philip E. Stanley, Extraction of Adenosine Triphosphate from Microbial and Somatic Cells, Methods in Enzymology, 1986, pp. 14-22, vol. 133, Academic Press, Inc. United States.

(Continued)

*Primary Examiner*—Ralph Gitomer
(74) *Attorney, Agent, or Firm*—Richard J. Long

(57) ABSTRACT

Methods, devices and systems are provided for detection of adenosine triphosphate (ATP) in samples using the luciferin-luciferase reaction. An aspect of the invention includes a low molarity and low pH composition for use in detecting the presence of ATP. The low molarity and low pH composition can be used in combination with methods for reading, calculating and interpreting luminescence generated by the ATP-luciferin-luciferase reaction. Both the low molarity, low pH composition and the methods for reading, calculating and interpreting luminescence can be used with a single service hygiene monitoring format.

24 Claims, 16 Drawing Sheets

OTHER PUBLICATIONS

Sharon R. Ford & Franklin R. Leach, Improvements in the Application of Firefly Luciferase Assays, Methods in Molecular Biology, Bioluminescence Methods and Protocols, pp. 3-20, Humana Press, Totowa, New Jersey, vol. 102, no date given.

A. Lundin, Extraction and Automatic Luminometric Assay of ATP, ADP and AMP, Analytical Applications of Bioluminescence and Chemiluminescence, 1984, pp. 491-501, Academic Press Inc. (Harcourt Brace Jovanovich Publishers), New York.

Maj-Rita Siro, Henrik Romar & Timo Lovgren Continuous Flow Method for Extraction and Bioluminescence Assay of ATP in Baker's Yeast, European Journal of Applied Microbiology and Biotechnology, 1982, pp. 258-264, vol. 15, Springer-Veriag Finland.

Larry J. Kricka & Marlene Deluca, Effect of Solvents on the Catalytic Activity of Firefly Luciferase, Archives of BioChemistry and BioPhysics, 1982, vol. 217, No. 2, Academic Press Inc. USA pp. 674-681.

W.D. McElroy & H.H. Seliger, Mechanisms of Bioluminescent Reactions, A Symposium on Light and Life, 1961, pp. 219-257 The John Hopkins Press, United States.

* cited by examiner

Figure 1 A
Figure 1 B
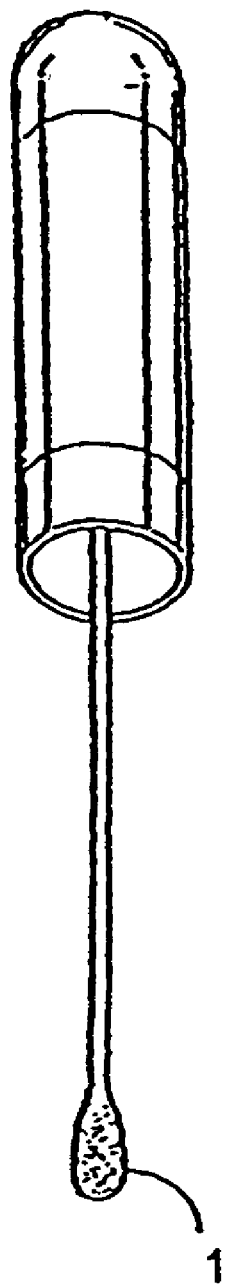
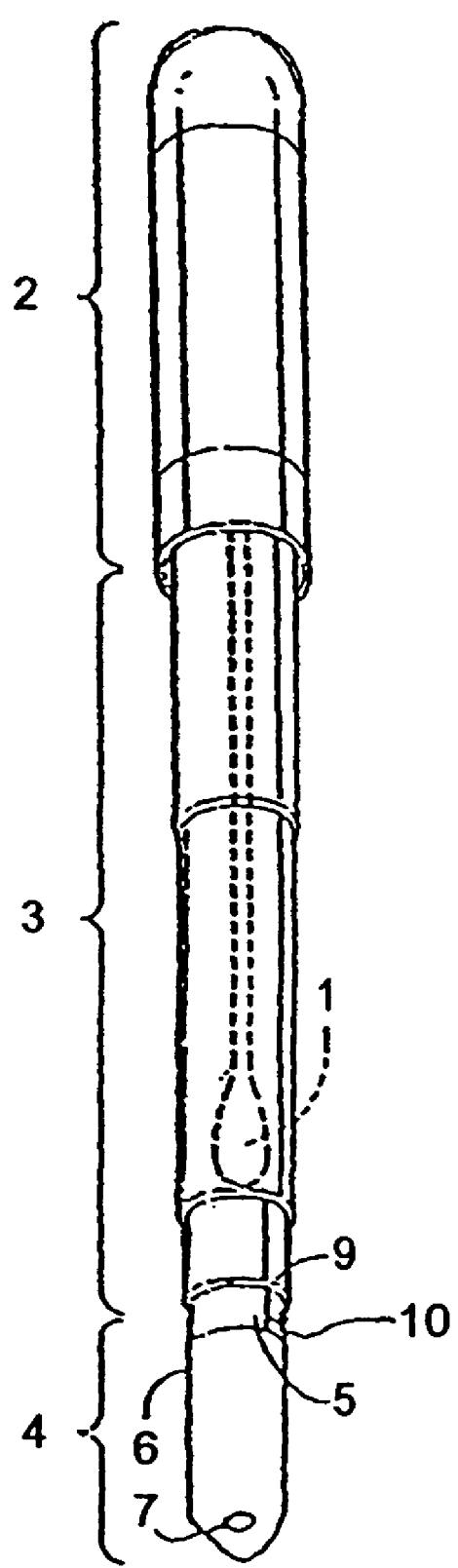

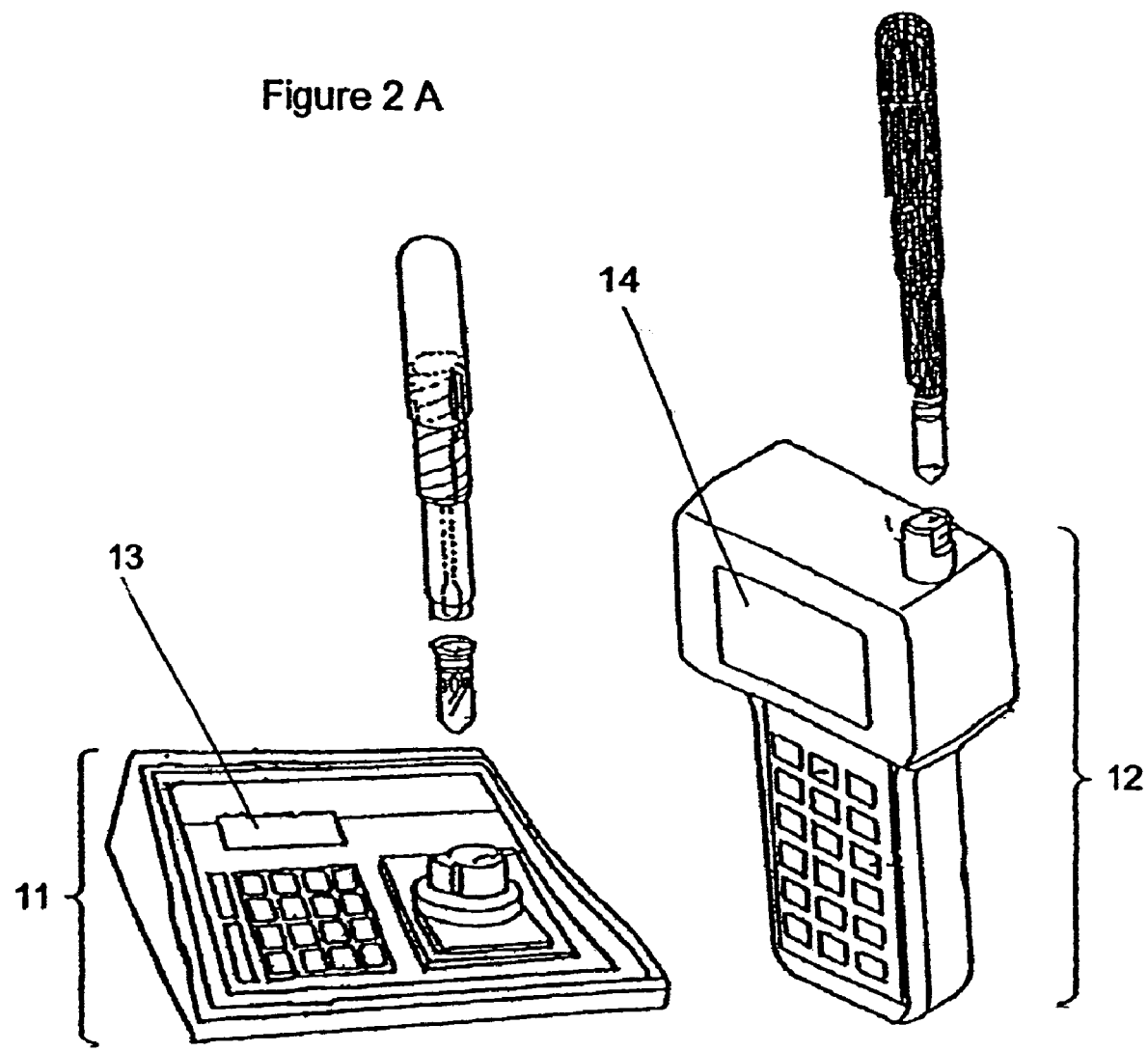

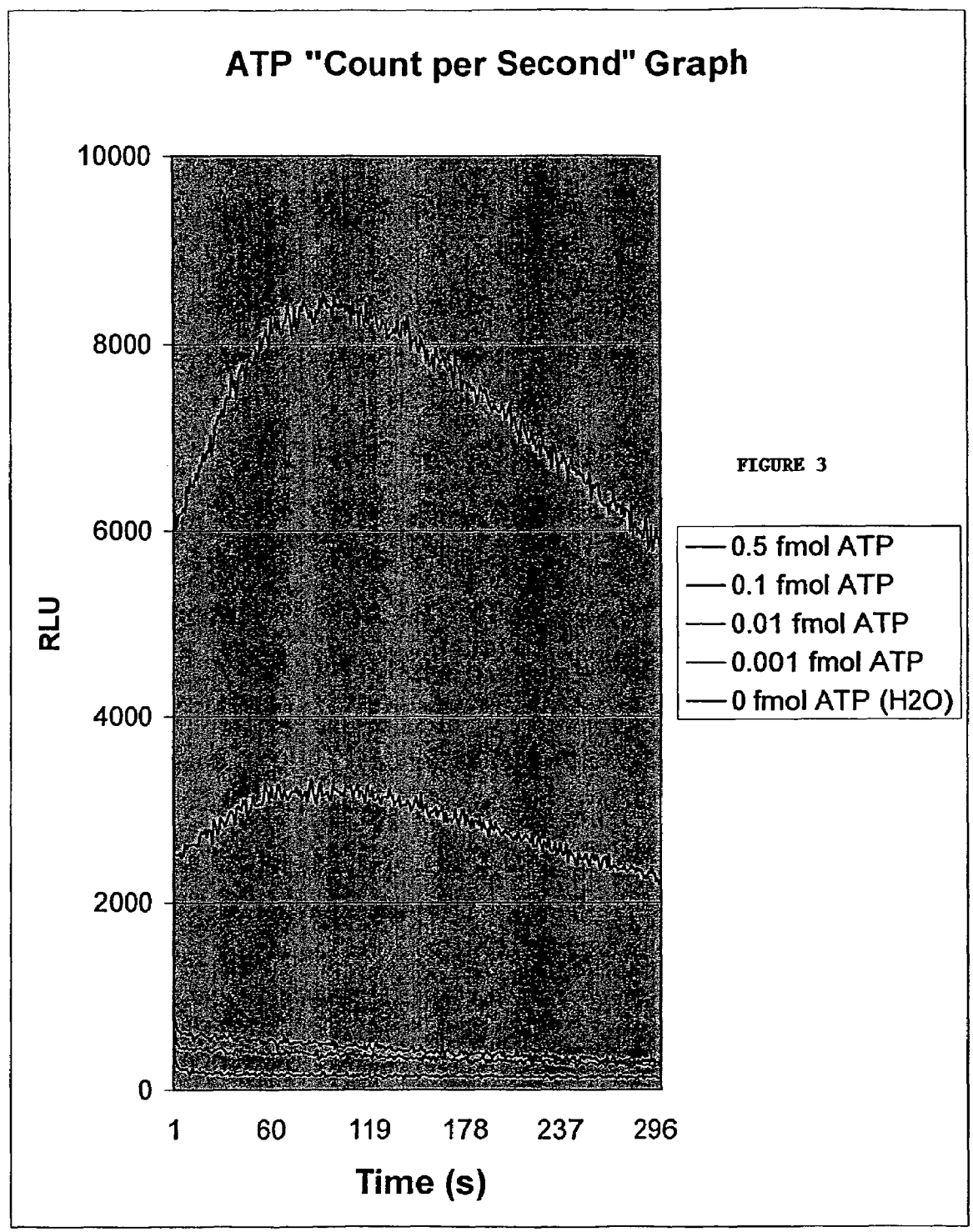

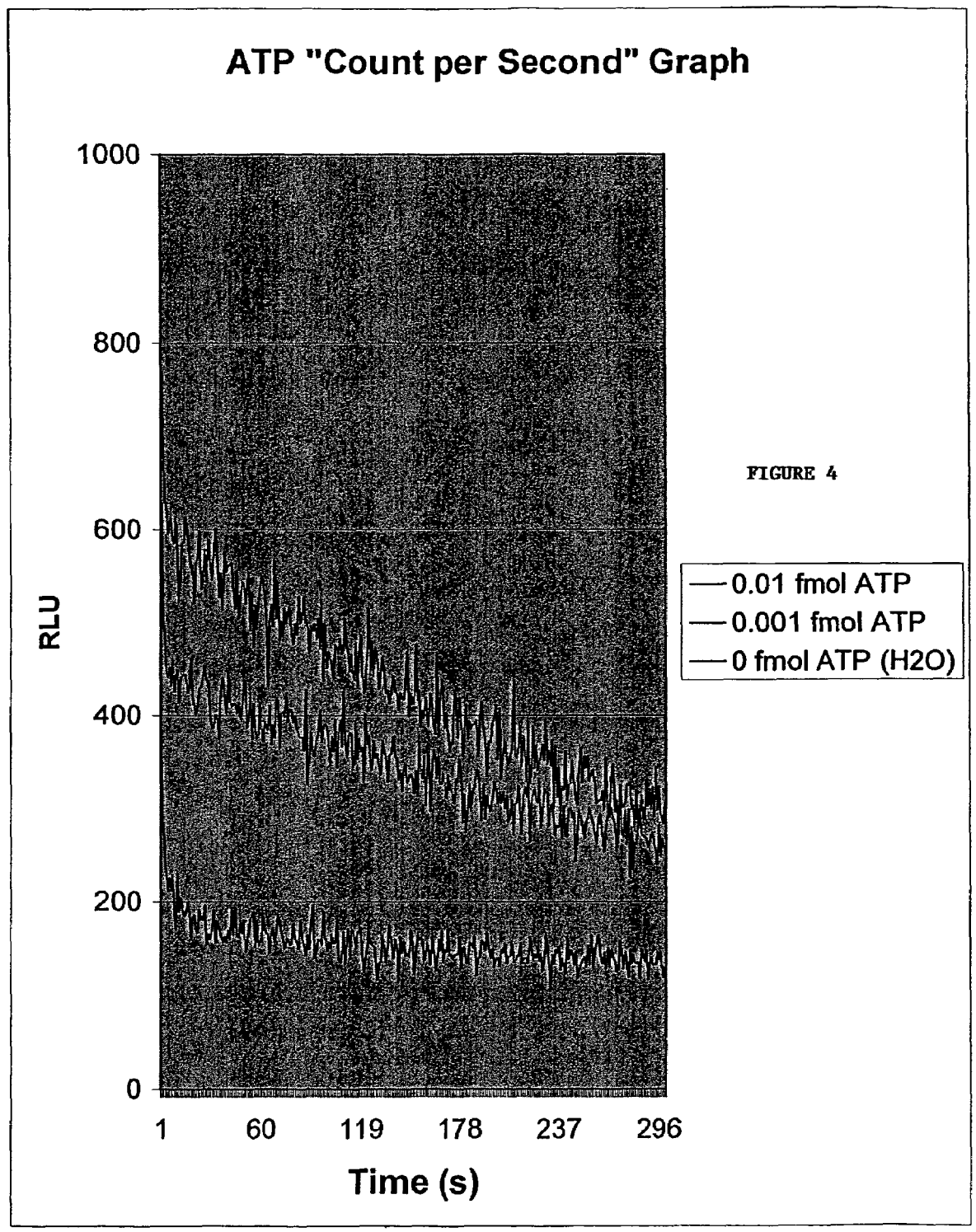

FIGURE 5A: Power Curve Fit
y = 1.2539 * x^(1.183); R = 0.99914
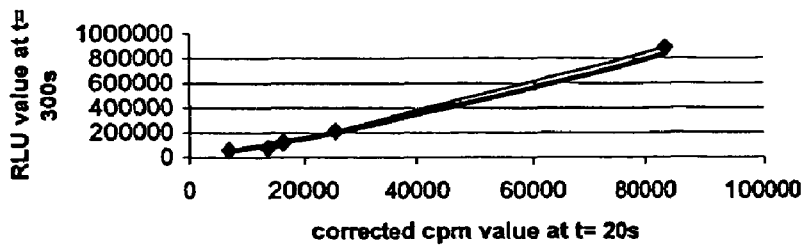
FIGURE 5B: Exponential Curve Fit
y = 59597 * e^(3.3426E-05x); R = 0.99357
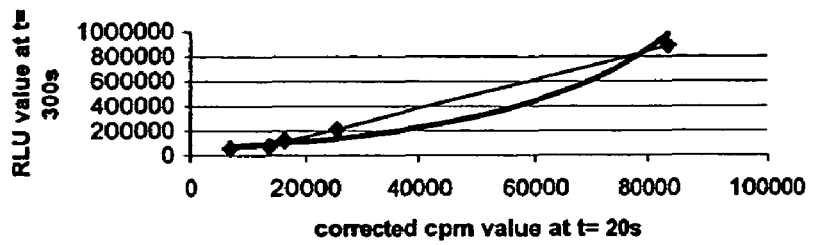
FIGURE 5C: Linear Trend Fit
y = 11.261x - 60594; R = 0.99805
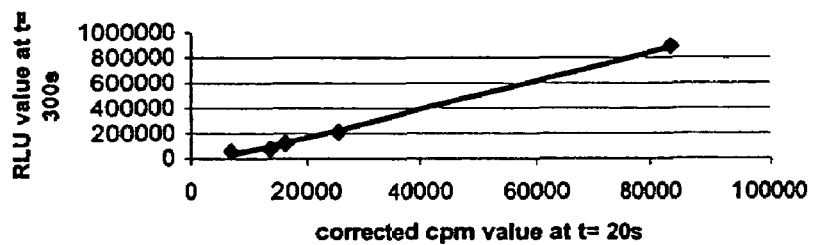
FIGURE 5D: Polynomial Curve Fit
y = 3.9039E-05x^2 + 7.5027x -13737; R = 0.99909
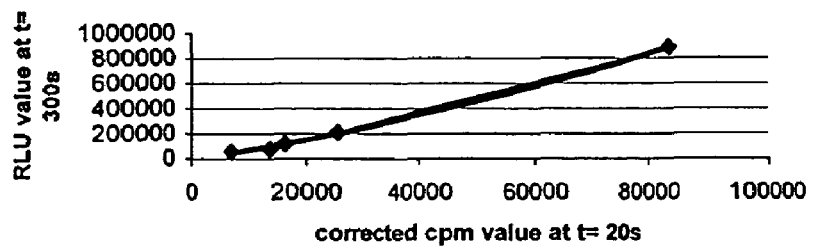

FIGURE 6: POWER CURVE ANALYSIS

|              |              | Col 1 | Col 2  | Col 3 | Col 4 | Col 5  | Col 6 |
|--------------|--------------|-------|--------|-------|-------|--------|-------|
| BLANKS   |              |       |        |       |       |        |       |
|              | 1 LUM-T      | 3259  | 195540 | 7550  | 64535 | 48513  | -24.8 |
|              | 2 #7339      | 3024  | 181440 | 7005  | 53316 | 44403  | -16.7 |
|              | 3 (CF=259)   | 3818  | 229080 | 8845  | 59786 | 58505  | -2.1  |
|              | 4            | 2498  | 149880 | 5787  | 50397 | 35419  | -29.7 |
|              | 5            | 3745  | 224700 | 8676  | 68279 | 57184  | -16.2 |
|              | 6            | 3042  | 182520 | 7047  | 55257 | 44716  | -19.1 |
|              | 7 LUM-T      | 3882  | 232920 | 8230  | 56105 | 53729  | -4.2  |
|              | 8 #7384      | 2874  | 172440 | 6093  | 52861 | 37648  | -28.8 |
|              | 9 (CF=283)   | 3387  | 203220 | 7181  | 61378 | 45722  | -25.5 |
|              | 10           | 3290  | 197400 | 6975  | 54922 | 44177  | -19.6 |
|              | 11           | 3346  | 200760 | 7094  | 62904 | 45068  | -28.4 |
|              | 12           | 3240  | 194400 | 6869  | 61180 | 43384  | -29.1 |
|              | *avg:*       | 3284  | 197025 | 7279  | 58410 |        |       |
|              | *stdev:*     | 403   | 24166  | 927   | 5409  |        |       |
|              | *avg + 3 stdev* | 4492 | 269522 | 10059 | 74638 |        |       |
| 0.005 fmol ATP |        |       |        |       |       |        |       |
|              | 1 LUM-T      | 5506  | 330360 | 12755 | 75704 | 90218  | 19.2  |
|              | 2 #7339      | 6420  | 385200 | 14873 | 78572 | 108192 | 37.7  |
|              | 3 (CF=259)   | 6647  | 398820 | 15398 | 82392 | 112732 | 36.8  |
|              | 4 LUM-T      | 6056  | 363360 | 12840 | 88060 | 90924  | 3.3   |
|              | 5 #7384      | 6373  | 382380 | 13512 | 85657 | 96581  | 12.8  |
|              | 6 (CF=283)   | 5314  | 318840 | 11266 | 74310 | 77898  | 4.8   |
|              | 7            | 7295  | 437700 | 15466 | 93046 | 113321 | 21.8  |
|              | 8            | 5448  | 326880 | 11551 | 79136 | 80227  | 1.4   |
|              | 9            | 5075  | 304500 | 10760 | 74889 | 73771  | -1.5  |
|              | *avg:*       | 6015  | 360893 | 13158 | 81307 |        |       |
|              | *stdev:*     | 732   | 43923  | 1789  | 6493  |        |       |

FIGURE 7: POWER CURVE ANALYSIS

0.01 fmol ATP

| | | Col 1 | Col 2 | Col 3 | Col 4 | Col 5 | Col 6 |
|---|---|---|---|---|---|---|---|
| 1 | LUM-T | 6981 | 418860 | 16172 | 111345 | 119464 | 7.3 |
| 2 | #7339 | 7250 | 435000 | 16795 | 118816 | 124929 | 5.1 |
| 3 | (CF=259) | 7343 | 440580 | 17011 | 127213 | 126827 | -0.3 |
| 4 | LUM-T | 8120 | 487200 | 17216 | 126570 | 128634 | 1.6 |
| 5 | #7384 | 9688 | 581280 | 20540 | 142214 | 158514 | 11.5 |
| 6 | (CF=283) | 11045 | 662700 | 23417 | 147097 | 185105 | 25.8 |
| 7 | | 7587 | 455220 | 16086 | 105190 | 118707 | 12.8 |
| 8 | | 9963 | 597780 | 21123 | 165578 | 163851 | -1.0 |
| 9 | | 8307 | 498420 | 17612 | 124534 | 132146 | 6.1 |
| *avg:* | | 8476 | 508560 | 18441 | 129840 | | |
| *stdev:* | | 1425 | 85506 | 2598 | 18858 | | |

0.1 fmol ATP

| | | Col 1 | Col 2 | Col 3 | Col 4 | Col 5 | Col 6 |
|---|---|---|---|---|---|---|---|
| 1 | LUM-T | 9747 | 584820 | 22580 | 202721 | 177303 | -12.5 |
| 2 | #7339 | 12527 | 751620 | 29020 | 241183 | 238581 | -1.1 |
| 3 | (CF=259) | 10118 | 607080 | 23439 | 188379 | 185314 | -1.6 |
| *avg:* | | 10797 | 647840 | 25013 | 210761 | | |
| *stdev:* | | 1509 | 90563 | 3497 | 27305 | | |

1 fmol ATP

| | | Col 1 | Col 2 | Col 3 | Col 4 | Col 5 | Col 6 |
|---|---|---|---|---|---|---|---|
| 1 | LUM-T | 40352 | 2421120 | 93480 | 935905 | 951964 | 1.7 |
| 2 | #7339 | 36668 | 2200080 | 84945 | 1026771 | 850029 | -17.2 |
| 3 | (CF=259) | 31338 | 1880280 | 72598 | 698156 | 705886 | 1.1 |
| *avg:* | | 36119 | 2167160 | 83674 | 886944 | | |
| *stdev:* | | 4532 | 271919 | 10499 | 169690 | | |

FIGURE 8: EXPONENTIAL CURVE ANALYSIS

|  | | Col 1 | Col 2 | Col 3 | Col 4 | Col 5 | Col 6 |
|---|---|---|---|---|---|---|---|
| BLANKS | | | | | | | |
| 1 | LUM-T | 3259 | 195540 | 7550 | 64535 | 74746 | 15.8 |
| 2 | #7339 | 3024 | 181440 | 7005 | 53316 | 73535 | 37.9 |
| 3 | (CF=259) | 3818 | 229080 | 8845 | 59786 | 77707 | 30.0 |
| 4 | | 2498 | 149880 | 5787 | 50397 | 70896 | 40.7 |
| 5 | | 3745 | 224700 | 8676 | 68279 | 77314 | 13.2 |
| 6 | | 3042 | 182520 | 7047 | 55257 | 73627 | 33.2 |
| 7 | LUM-T | 3882 | 232920 | 8230 | 56105 | 76288 | 36.0 |
| 8 | #7384 | 2874 | 172440 | 6093 | 52861 | 71551 | 35.4 |
| 9 | (CF=283) | 3387 | 203220 | 7181 | 61378 | 73924 | 20.4 |
| 10 | | 3290 | 197400 | 6975 | 54922 | 73469 | 33.8 |
| 11 | | 3346 | 200760 | 7094 | 62904 | 73731 | 17.2 |
| 12 | | 3240 | 194400 | 6869 | 61180 | 73236 | 19.7 |
| *avg:* | | 3284 | 197025 | 7279 | 58410 | | |
| *stdev:* | | 403 | 24166 | 927 | 5409 | | |
| *avg + 3 stdev* | | 4492 | 269522 | 10059 | 74638 | | |
| 0.005 fmol ATP | | | | | | | |
| 1 | LUM-T | 5506 | 330360 | 12755 | 75704 | 87380 | 15.4 |
| 2 | #7339 | 6420 | 385200 | 14873 | 78572 | 93110 | 18.5 |
| 3 | (CF=259) | 6647 | 398820 | 15398 | 82392 | 94591 | 14.8 |
| 4 | LUM-T | 6056 | 363360 | 12840 | 88060 | 87601 | -0.5 |
| 5 | #7384 | 6373 | 382380 | 13512 | 85657 | 89385 | 4.4 |
| 6 | (CF=283) | 5314 | 318840 | 11266 | 74310 | 83563 | 12.5 |
| 7 | | 7295 | 437700 | 15466 | 93046 | 94784 | 1.9 |
| 8 | | 5448 | 326880 | 11551 | 79136 | 84278 | 6.5 |
| 9 | | 5075 | 304500 | 10760 | 74889 | 82302 | 9.9 |
| *avg:* | | 6015 | 360893 | 13158 | 81307 | | |
| *stdev:* | | 732 | 43923 | 1789 | 6493 | | |

FIGURE 9: EXPONENTIAL CURVE ANALYSIS

|  | Col 1 | Col 2 | Col 3 | Col 4 | Col 5 | Col 6 |
|---|---|---|---|---|---|---|
| 0.01 fmol ATP | | | | | | |
| 1 LUM-T | 6981 | 418860 | 16172 | 111345 | 96812 | -13.1 |
| 2 #7339 | 7250 | 435000 | 16795 | 118816 | 98639 | -17.0 |
| 3 (CF=259) | 7343 | 440580 | 17011 | 127213 | 99279 | -22.0 |
| 4 LUM-T | 8120 | 487200 | 17216 | 126570 | 99890 | -21.1 |
| 5 #7384 | 9688 | 581280 | 20540 | 142214 | 110366 | -22.4 |
| 6 (CF=283) | 11045 | 662700 | 23417 | 147097 | 120315 | -18.2 |
| 7 | 7587 | 455220 | 16086 | 105190 | 96561 | -8.2 |
| 8 | 9963 | 597780 | 21123 | 165578 | 112314 | -32.2 |
| 9 | 8307 | 498420 | 17612 | 124534 | 101085 | -18.8 |
| avg: | 8476 | 508560 | 18441 | 129840 | | |
| stdev: | 1425 | 85506 | 2598 | 18858 | | |
| 0.1 fmol ATP | | | | | | |
| 1 LUM-T | 9747 | 584820 | 22580 | 202721 | 117331 | -42.1 |
| 2 #7339 | 12527 | 751620 | 29020 | 241183 | 142338 | -41.0 |
| 3 (CF=259) | 10118 | 607080 | 23439 | 188379 | 120396 | -36.1 |
| avg: | 10797 | 647840 | 25013 | 210761 | | |
| stdev: | 1509 | 90563 | 3497 | 27305 | | |
| 1 fmol ATP | | | | | | |
| 1 LUM-T | 40352 | 2421120 | 93480 | 935905 | 984360 | 5.2 |
| 2 #7339 | 36668 | 2200080 | 84945 | 1026771 | 762011 | -25.8 |
| 3 (CF=259) | 31338 | 1880280 | 72598 | 698156 | 526123 | -24.6 |
| avg: | 36119 | 2167160 | 83674 | 886944 | | |
| stdev: | 4532 | 271919 | 10499 | 169690 | | |

FIGURE 10: LINEAR CURVE ANALYSIS

|  | Col 1 | Col 2 | Col 3 | Col 4 | Col 5 | Col 6 |
|---|---|---|---|---|---|---|
| BLANKS | | | | | | |
| 1 LUM-T | 3259 | 195540 | 7550 | 64535 | 24424 | -62.2 |
| 2 #7339 | 3024 | 181440 | 7005 | 53316 | 18294 | -65.7 |
| 3 (CF=259) | 3818 | 229080 | 8845 | 59786 | 39007 | -34.8 |
| 4 | 2498 | 149880 | 5787 | 50397 | 4572 | -90.9 |
| 5 | 3745 | 224700 | 8676 | 68279 | 37103 | -45.7 |
| 6 | 3042 | 182520 | 7047 | 55257 | 18763 | -66.0 |
| 7 LUM-T | 3882 | 232920 | 8230 | 56105 | 32088 | -42.8 |
| 8 #7384 | 2874 | 172440 | 6093 | 52861 | 8022 | -84.8 |
| 9 (CF=283) | 3387 | 203220 | 7181 | 61378 | 20270 | -67.0 |
| 10 | 3290 | 197400 | 6975 | 54922 | 17954 | -67.3 |
| 11 | 3346 | 200760 | 7094 | 62904 | 19291 | -69.3 |
| 12 | 3240 | 194400 | 6869 | 61180 | 16761 | -72.6 |
| *avg:* | 3284 | 197025 | 7279 | 58410 | | |
| *stdev:* | 403 | 24166 | 927 | 5409 | | |
| *avg + 3 stdev* | 4492 | 269522 | 10059 | 74638 | | |
| 0.005 fmol ATP | | | | | | |
| 1 LUM-T | 5506 | 330360 | 12755 | 75704 | 83042 | 9.7 |
| 2 #7339 | 6420 | 385200 | 14873 | 78572 | 106886 | 36.0 |
| 3 (CF=259) | 6647 | 398820 | 15398 | 82392 | 112808 | 36.9 |
| 4 LUM-T | 6056 | 363360 | 12840 | 88060 | 83992 | -4.6 |
| 5 #7384 | 6373 | 382380 | 13512 | 85657 | 91561 | 6.9 |
| 6 (CF=283) | 5314 | 318840 | 11266 | 74310 | 66277 | -10.8 |
| 7 | 7295 | 437700 | 15466 | 93046 | 113573 | 22.1 |
| 8 | 5448 | 326880 | 11551 | 79136 | 69477 | -12.2 |
| 9 | 5075 | 304500 | 10760 | 74889 | 60571 | -19.1 |
| *avg:* | 6015 | 360893 | 13158 | 81307 | | |
| *stdev:* | 732 | 43923 | 1789 | 6493 | | |

FIGURE 11: LINEAR CURVE ANALYSIS

| | | Col 1 | Col 2 | Col 3 | Col 4 | Col 5 | Col 6 |
|---|---|---|---|---|---|---|---|
| 0.01 fmol ATP | | | | | | | |
| | 1 LUM-T | 6981 | 418860 | 16172 | 111345 | 121521 | 9.1 |
| | 2 #7339 | 7250 | 435000 | 16795 | 118816 | 128539 | 8.2 |
| | 3 (CF=259) | 7343 | 440580 | 17011 | 127213 | 130965 | 2.9 |
| | 4 LUM-T | 8120 | 487200 | 17216 | 126570 | 133270 | 5.3 |
| | 5 #7384 | 9688 | 581280 | 20540 | 142214 | 170706 | 20.0 |
| | 6 (CF=283) | 11045 | 662700 | 23417 | 147097 | 203104 | 38.1 |
| | 7 | 7587 | 455220 | 16086 | 105190 | 120545 | 14.6 |
| | 8 | 9963 | 597780 | 21123 | 165578 | 177272 | 7.1 |
| | 9 | 8307 | 498420 | 17612 | 124534 | 137735 | 10.6 |
| | *avg:* | 8476 | 508560 | 18441 | 129840 | | |
| | *stdev:* | 1425 | 85506 | 2598 | 18858 | | |
| 0.1 fmol ATP | | | | | | | |
| | 1 LUM-T | 9747 | 584820 | 22580 | 202721 | 193679 | -4.5 |
| | 2 #7339 | 12527 | 751620 | 29020 | 241183 | 266201 | 10.4 |
| | 3 (CF=259) | 10118 | 607080 | 23439 | 188379 | 203357 | 8.0 |
| | *avg:* | 10797 | 647840 | 25013 | 210761 | | |
| | *stdev:* | 1509 | 90563 | 3497 | 27305 | | |
| 1 fmol ATP | | | | | | | |
| | 1 LUM-T | 40352 | 2421120 | 93480 | 935905 | 992079 | 6.0 |
| | 2 #7339 | 36668 | 2200080 | 84945 | 1026771 | 895974 | -12.7 |
| | 3 (CF=259) | 31338 | 1880280 | 72598 | 698156 | 756929 | 8.4 |
| | *avg:* | 36119 | 2167160 | 83674 | 886944 | | |
| | *stdev:* | 4532 | 271919 | 10499 | 169690 | | |

FIGURE 12: POLYNOMIAL CURVE ANALYSIS

| BLANKS | | Col 1 | Col 2 | Col 3 | Col 4 | Col 5 | Col 6 |
|---|---|---|---|---|---|---|---|
| 1 | LUM-T | 3259 | 195540 | 7550 | 64535 | 45187 | -30.0 |
| 2 | #7339 | 3024 | 181440 | 7005 | 53316 | 40785 | -23.5 |
| 3 | (CF=259) | 3818 | 229080 | 8845 | 59786 | 55752 | -6.7 |
| 4 | | 2498 | 149880 | 5787 | 50397 | 31020 | -38.4 |
| 5 | | 3745 | 224700 | 8676 | 68279 | 54365 | -20.4 |
| 6 | | 3042 | 182520 | 7047 | 55257 | 41122 | -25.6 |
| 7 | LUM-T | 3882 | 232920 | 8230 | 56105 | 50723 | -9.6 |
| 8 | #7384 | 2874 | 172440 | 6093 | 52861 | 33464 | -36.7 |
| 9 | (CF=283) | 3387 | 203220 | 7181 | 61378 | 42202 | -31.2 |
| 10 | | 3290 | 197400 | 6975 | 54922 | 40542 | -26.2 |
| 11 | | 3346 | 200760 | 7094 | 62904 | 41500 | -34.0 |
| 12 | | 3240 | 194400 | 6869 | 61180 | 39688 | -35.1 |
| avg: | | 3284 | 197025 | 7279 | 58410 | | |
| stdev: | | *403* | *24166* | *927* | *5409* | | |
| avg + 3 stdev | | 4492 | 269522 | 10059 | 74638 | | |

0.005 fmol ATP

| | | Col 1 | Col 2 | Col 3 | Col 4 | Col 5 | Col 6 |
|---|---|---|---|---|---|---|---|
| 1 | LUM-T | 5506 | 330360 | 12755 | 75704 | 88469 | 16.9 |
| 2 | #7339 | 6420 | 385200 | 14873 | 78572 | 106695 | 35.8 |
| 3 | (CF=259) | 6647 | 398820 | 15398 | 82392 | 111277 | 35.1 |
| 4 | LUM-T | 6056 | 363360 | 12840 | 88060 | 89189 | 1.3 |
| 5 | #7384 | 6373 | 382380 | 13512 | 85657 | 94940 | 10.8 |
| 6 | (CF=283) | 5314 | 318840 | 11266 | 74310 | 75869 | 2.1 |
| 7 | | 7295 | 437700 | 15466 | 93046 | 111871 | 20.2 |
| 8 | | 5448 | 326880 | 11551 | 79136 | 78260 | -1.1 |
| 9 | | 5075 | 304500 | 10760 | 74889 | 71621 | -4.4 |
| avg: | | 6015 | 360893 | 13158 | 81307 | | |
| stdev: | | *732* | *43923* | *1789* | *6493* | | |

FIGURE 13: POLYNOMIAL CURVE ANALYSIS

0.01 fmol ATP

|   | Col 1 | Col 2 | Col 3 | Col 4 | Col 5 | Col 6 |
|---|---|---|---|---|---|---|
| 1 LUM-T | 6981 | 418860 | 16172 | 111345 | 118060 | 6.0 |
| 2 #7339 | 7250 | 435000 | 16795 | 118816 | 123557 | 4.0 |
| 3 (CF=259) | 7343 | 440580 | 17011 | 127213 | 125465 | -1.4 |
| 4 LUM-T | 8120 | 487200 | 17216 | 126570 | 127281 | 0.6 |
| 5 #7384 | 9688 | 581280 | 20540 | 142214 | 157243 | 10.6 |
| 6 (CF=283) | 11045 | 662700 | 23417 | 147097 | 183888 | 25.0 |
| 7 | 7587 | 455220 | 16086 | 105190 | 117298 | 11.5 |
| 8 | 9963 | 597780 | 21123 | 165578 | 162589 | -1.8 |
| 9 | 8307 | 498420 | 17612 | 124534 | 130808 | 5.0 |
| *avg:* | 8476 | 508560 | 18441 | 129840 | | |
| *stdev:* | 1425 | 85506 | 2598 | 18858 | | |

0.1 fmol ATP

|   | Col 1 | Col 2 | Col 3 | Col 4 | Col 5 | Col 6 |
|---|---|---|---|---|---|---|
| 1 LUM-T | 9747 | 584820 | 22580 | 202721 | 176068 | -13.1 |
| 2 #7339 | 12527 | 751620 | 29020 | 241183 | 237679 | -1.5 |
| 3 (CF=259) | 10118 | 607080 | 23439 | 188379 | 184098 | -2.3 |
| *avg:* | 10797 | 647840 | 25013 | 210761 | | |
| *stdev:* | 1509 | 90563 | 3497 | 27305 | | |

1 fmol ATP

|   | Col 1 | Col 2 | Col 3 | Col 4 | Col 5 | Col 6 |
|---|---|---|---|---|---|---|
| 1 LUM-T | 40352 | 2421120 | 93480 | 935905 | 1037149 | 10.8 |
| 2 #7339 | 36668 | 2200080 | 84945 | 1026771 | 912208 | -11.2 |
| 3 (CF=259) | 31338 | 1880280 | 72598 | 698156 | 741759 | 6.2 |
| *avg:* | 36119 | 2167160 | 83674 | 886944 | | |
| *stdev:* | 4532 | 271919 | 10499 | 169690 | | |

FIGURE 14: AVERAGE OF EXPONENTIAL AND POWER CURVES

| BLANKS | | Col 1 | Col 2 | Col 3 | Col 4 | Col 5 | Col 6 |
|---|---|---|---|---|---|---|---|
| 1 | LUM-T | 3259 | 195540 | 7550 | 64535 | 61630 | -4.5 |
| 2 | #7339 | 3024 | 181440 | 7005 | 53316 | 58969 | 10.6 |
| 3 | (CF=259) | 3818 | 229080 | 8845 | 59786 | 68106 | 13.9 |
| 4 | | 2498 | 149880 | 5787 | 50397 | 53157 | 5.5 |
| 5 | | 3745 | 224700 | 8676 | 68279 | 67249 | -1.5 |
| 6 | | 3042 | 182520 | 7047 | 55257 | 59172 | 7.1 |
| 7 | LUM-T | 3882 | 232920 | 8230 | 56105 | 65008 | 15.9 |
| 8 | #7384 | 2874 | 172440 | 6093 | 52861 | 54599 | 3.3 |
| 9 | (CF=283) | 3387 | 203220 | 7181 | 61378 | 59823 | -2.5 |
| 10 | | 3290 | 197400 | 6975 | 54922 | 58823 | 7.1 |
| 11 | | 3346 | 200760 | 7094 | 62904 | 59399 | -5.6 |
| 12 | | 3240 | 194400 | 6869 | 61180 | 58310 | -4.7 |
| *avg:* | | 3284 | 197025 | 7279 | 58410 | | |
| *stdev:* | | 403 | 24166 | 927 | 5409 | | |
| *avg +* | | | | | | | |
| *3 stdev* | | 4492 | 269522 | 10059 | 74638 | | |

| 0.005 fmol ATP | | | | | | | |
|---|---|---|---|---|---|---|---|
| 1 | LUM-T | 5506 | 330360 | 12755 | 75704 | 88799 | 17.3 |
| 2 | #7339 | 6420 | 385200 | 14873 | 78572 | 100651 | 28.1 |
| 3 | (CF=259) | 6647 | 398820 | 15398 | 82392 | 103661 | 25.8 |
| 4 | LUM-T | 6056 | 363360 | 12840 | 88060 | 89262 | 1.4 |
| 5 | #7384 | 6373 | 382380 | 13512 | 85657 | 92983 | 8.6 |
| 6 | (CF=283) | 5314 | 318840 | 11266 | 74310 | 80730 | 8.6 |
| 7 | | 7295 | 437700 | 15466 | 93046 | 104053 | 11.8 |
| 8 | | 5448 | 326880 | 11551 | 79136 | 82253 | 3.9 |
| 9 | | 5075 | 304500 | 10760 | 74889 | 78036 | 4.2 |
| *avg:* | | 6015 | 360893 | 13158 | 81307 | | |
| *stdev:* | | 732 | 43923 | 1789 | 6493 | | |

FIGURE 15: AVERAGE OF EXPONENTIAL AND POWER CURVES

|  | Col 1 | Col 2 | Col 3 | Col 4 | Col 5 | Col 6 |
|---|---|---|---|---|---|---|
| 0.01 fmol ATP | | | | | | |
| 1 LUM-T | 6981 | 418860 | 16172 | 111345 | 108138 | -2.9 |
| 2 #7339 | 7250 | 435000 | 16795 | 118816 | 111784 | -5.9 |
| 3 (CF=259) | 7343 | 440580 | 17011 | 127213 | 113053 | -11.1 |
| 4 LUM-T | 8120 | 487200 | 17216 | 126570 | 114262 | -9.7 |
| 5 #7384 | 9688 | 581280 | 20540 | 142214 | 134440 | -5.5 |
| 6 (CF=283) | 11045 | 662700 | 23417 | 147097 | 152710 | 3.8 |
| 7 | 7587 | 455220 | 16086 | 105190 | 107634 | 2.3 |
| 8 | 9963 | 597780 | 21123 | 165578 | 138082 | -16.6 |
| 9 | 8307 | 498420 | 17612 | 124534 | 116616 | -6.4 |
| avg: | 8476 | 508560 | 18441 | 129840 | | |
| stdev: | 1425 | 85506 | 2598 | 18858 | | |
| 0.1 fmol ATP | | | | | | |
| 1 LUM-T | 9747 | 584820 | 22580 | 202721 | 147317 | -27.3 |
| 2 #7339 | 12527 | 751620 | 29020 | 241183 | 190460 | -21.0 |
| 3 (CF=259) | 10118 | 607080 | 23439 | 188379 | 152855 | -18.9 |
| avg: | 10797 | 647840 | 25013 | 210761 | | |
| stdev: | 1509 | 90563 | 3497 | 27305 | | |
| 1 fmol ATP | | | | | | |
| 1 LUM-T | 40352 | 2421120 | 93480 | 935905 | 968162 | 3.4 |
| 2 #7339 | 36668 | 2200080 | 84945 | 1026771 | 806020 | -21.5 |
| 3 (CF=259) | 31338 | 1880280 | 72598 | 698156 | 616005 | -11.8 |
| avg: | 36119 | 2167160 | 83674 | 886944 | | |
| stdev: | 4532 | 271919 | 10499 | 169690 | | |

METHOD OF DETERMINING ALLERGENIC FOOD ON SURFACES

REFERENCE TO PRIOR APPLICATIONS

This application is based on and claims priority from U.S. Provisional Patent Application Ser. No. 60/469,707, filed May 12, 2003; U.S. Provisional Patent Application Ser. No. 60/497,422, filed Aug. 22, 2003; U.S. Provisional Patent Application Ser. No. 60/507,058, filed Sep. 29, 2003; and U.S. Provisional Patent Application Ser. No. 60/530,846, filed Dec. 17, 2003, all of which are hereby incorporated by reference.

FIELD OF THE INVENTION

The invention relates to detection of adenosine triphosphate (ATP) for hygiene monitoring.

BACKGROUND OF THE INVENTION

Determination of cleanliness in industrial and health care settings is important for maintaining good hygiene and sanitation. The surfaces of equipment used for food handling, storage or processing are major sources of microbial and allergen contamination. Microbial contamination can lead to decreased shelf life of products and, if pathogens are present, transmission of disease. Unexpected allergens on food contact surfaces may cause food to become contaminated. Such contamination has the potential to cause adverse reactions, such as an allergic reaction including hives, anaphylaxis and death, in sensitive people who consume or otherwise contact the contaminated food.

Historically, microbial culturing was used to determine the presence of microorganisms. However, culturing is time consuming and, therefore, the necessary "real time" feedback to sanitation and food preparation personnel is not available. As a result, food exposed to surfaces later found to contain potentially harmful microorganisms could enter the food supply.

During the 1990's various rapid and efficient test methods and devices were developed for the detection of contamination on surfaces. Some of these methods do not detect microbes directly but instead use markers such as adenosine triphosphate (ATP) that are indicative of either the presence of microbes or the existence of residual food contamination of a surface. One such apparatus is the POCKETSWAB-PLUS (POCKETSWAB is a registered trademark of Charm Sciences, Inc. of Lawrence, Massachusetts), which rapidly and efficiently detects ATP on surfaces. The POCKETSWAB apparatus detects ATP through the reaction of luciferin and luciferase, which, in the presence of ATP, generates luminescence (light). Luminescence generated is measured using a luminometer. Such ATP detection systems generally provide the user with an average reading of relative light units (RLU's) over a time period, for example 5 seconds.

Also during the late 1990's, allergen tests were developed to detect allergenic components of foods. These tests are typically ELISA (enzyme linked immunosorbent assay) based and require 30 minutes or more before a result is obtained. ELISA allergen tests have generally been more sensitive for detecting allergenic food residues than previously available ATP tests such as the POCKETSWAB.

Maximizing the sensitivity of ATP detection assays and systems, particularly single service ATP detection assays, could expand their usefulness. For example, an adequately sensitive ATP detection system could be used to rapidly screen a surface for food residue at the level of allergen test detection. For example, in the case of tests that detect peanut allergens, regulations require sensitivity of 5 parts per million peanut residue.

SUMMARY OF THE INVENTION

It is an object of this invention to provide a method, apparatus and system for improved detection of ATP in a sample. Said method includes adding a test sample to a solution to create a first admixture and then admixing said first admixture with reagents, for example luciferin and luciferase, to form a second admixture. In addition to luciferin and luciferase, said second admixture will include at least one buffer and, optionally, at least one detergent. In most cases, the detergent, for example benzalkonium chloride, will be provided in the solution to which the test sample is added to form the first admixture. The percentage of benzalkonium chloride in the solution is generally, for example, in the range of about 0.003% to about 0.01% benzalkonium chloride, for example about 0.005%. Generally, the second admixture will also include at least one co-factor for the luciferin-luciferase-ATP reaction, for example magnesium. In an example, the buffer, for example a phosphate buffer including partly, mostly or exclusively dibasic phosphate, is provided at a molar concentration of less than about 50 millimolar, for example about 0.2 millimolar to less than about 10 millimolar. Generally, the pH of the second admixture will be less than about 7.2. The reaction resulting from the creation of the second admixture generates luminescence. The luminescence generated is detected and used as an indication of sample ATP. It will be appreciated that although we generally refer to the solution as including the buffer and detergent in liquid from and the reagent, or reagent composition, as including the luciferin-luciferase in solid form such as in a tablet, it is also possible to have luciferin-luciferase in liquid form. Similarly, the buffer and detergent ingredients can be provided in solid form to be rehydrated during, or prior to, testing.

We have found that enhanced ATP sensitivity can be achieved using a luciferin-luciferase-ATP reaction occurring at a pH well below the previously taught optimum of pH 7.8. It is, therefore, an object of this invention to provide a method for detecting ATP, using the luciferin-luciferase-ATP reaction, that occurs at pH less than 7.8, for example about 6.5 to about 7.2. In an example, said invention includes contacting the sample, initially with a solution of pH about 6.9, for example a dibasic phosphate buffer containing benzalkonium chloride.

It is a further object of this invention to provide a method of detecting the total light generated from the ATP reaction during a relatively short time, for example about 5 to about 30 seconds, and, optionally, extrapolating, for example using a regression formula, to predict the light that would be generated over a longer period of time, for example 5 minutes. The combination of these methods, for detection and prediction, with the method for enhancing ATP sensitivity using, for example a low molarity, low pH phosphate buffer, allows increased ATP sensitivity, for example to the level useful for allergen detection.

It is another object of this invention to provide a test apparatus for improved detection of ATP in a test sample, by luminescence. The improvement in sensitivity is useful, for example, as an indicator of possible allergen contamination or as an indicator of relatively low levels of microbial contamination. The test apparatus can include a longitudinal housing having a one end and another end and a moveable probe within the housing to collect a test sample. Generally, a transparent closed bottom end extending from the one end of the housing will be used to detect the luminescence generated from the test sample. The test apparatus includes a solution into which the test sample is added to create an admixture. The solution generally includes a buffer, for example a phosphate buffer, at a concentration of less than about 50 millimolar, for example about 0.1 to about 10 millimolar dibasic phosphate buffer, and a detergent. The solution can be in a pH range of about 6.5 to about 7.0. The detergent can be, for example, benzalkonium chloride. The percentage of detergent relative to buffer can be about 0.01 to about 0.005 percent detergent. The volume of solution can vary. In a particular example, 300 microliters is used.

To generate light as an indicator of sample ATP, a reagent composition with which the admixture is combined to create a second admixture will generally include luciferin and luciferase. The second admixture can also generally include a co-factor such as magnesium and, in a particular example, will have a pH between about 6.7 to about 7.2.

It is a particular object of this invention to provide an easy to use all-in-one device for ATP detection at improved sensitivity levels. In one example of such a device a moveable probe is arranged to puncture at least one membrane seal which separates various mixtures, for example the solution from the reagent composition. In another example, the membrane seals surround a chamber in which the solution, or alternatively the reagent composition, can be provided.

It is another object of this invention to improve sensitivity of hygiene monitoring methods, such as those using the ATP-luciferin-luciferase reaction, by providing improved methods for measuring and interpreting luminescence output. In one such method, a sample is added to reagents, such as luciferin-luciferase, that generates luminescence in the presence of ATP. The sample and reagents are combined in a container that is inserted into a luminescence detector, such as a photomultiplier based detector or a photodiode based detector. The luminescence detector detects, quantifies, and stores in memory, the total luminescence output from said reagents, within the container, generated during a predetermined period of time. Total luminescence generated is detected, for example by detecting RLU's generated per second and adding together the total RLU's generated, for example, during a time period of about 5 seconds to about 60 seconds or more, for example about 20 seconds. That total can be used as the result or, alternatively, used to predict the total luminescence that would be generated during a longer period of time, for example during 5 minutes. By using a shorter count, for example, a 20 second count, to accurately extrapolate (predict) a 5 minute count, sensitivity can be increased. The program used for calculating or predicting can be internal to the luminescence detector or external, for example in an accessory computer.

To predict the RLU's that would be generated, during for example a 5 minute count, a variety of possible formulas can be used such as a linear or non-linear regression formula. Examples of such non-linear regression formulas include power curve formulas, exponential curve formulas and polynomial curve formulas. In addition, it is possible to predict using the average results from two or more formulas.

The described method for predicting RLU counts can be used in combination with the previously described method for using low molarity, low pH reagents. For example, this method includes reacting the reagents for luminescence generation in a solution. The solution can include at least one buffer, for example, a phosphate buffer including partly, mostly or substantially all dibasic phosphate. The total buffer concentration can be, for example, less than about 20 millimolar. In an example, the concentration is less than 5 millimolar, for example, in the range of about 0.2 to about 3 millimolar. The solution can also include a detergent such as benzalkonium chloride, for example about 0.01 percent or less of said solution. In an example, the percentage of benzalkonium chloride is approximately 0.005 percent.

It is also an object of this invention to provide a complete test system to sensitively detect ATP in a test sample, by luminescence. Such a complete test system, in one example, includes a test apparatus with a housing having a one end and another end. The housing includes within it a moveable probe to collect a test sample and arranged to puncture at least one membrane seal, for example membrane seals used to seal a liquid within a reagent chamber. The bottom end of the test apparatus is transparent, closed and extended from the one end of the housing. The transparent bottom end is the end through which generated luminescence is detected by the luminescence detector. The test apparatus includes a solution, for example a solution sealed in a chamber by the membrane seals, into which a sample is admixed creating a first admixture. The solution can include, for example phosphate buffer having a molarity of less than about 1 millimolar; and less than about 0.01 percent benzalkonium chloride. The first admixture can be released from the sealed chamber to contact reagents such as luciferin and luciferase to create a second admixture that reacts to generate luminescence. A luminescence detector for reading luminescence output can be programmed to detect and store in memory, the total luminescence generated, during a predetermined period of time. The luminescence detector, or a related instrument, can then be used to calculate a predicted total luminescence that would be generated during a period of time longer than the predetermined period of time. That prediction is used as the result. In a particular example, the second admixture has a pH of about 7.2 and a total buffer molarity of less than about 10 millimolar.

Examples of potential applications for the herein described sensitive ATP detection methods, devices and systems include testing water, particularly spring water or other bottled water, for contamination and testing water to be used by pharmaceutical companies to meet USPC standards. Another application is for dairies that share production lines and packaging equipment between water and dairy packaging where dairy residue in water is an allergenic concern. Still another application is as an indirect method for screening a surface for allergenic foods; a positive result would tell the user that food residue ATP may exist at the level of allergen test detection. Another potential application includes a test to detect the potential for contamination on surfaces or, for example, in drinking water. In one embodiment, a sample, for example a water sample, is filtered to concentrate organic matter and then the concentrate is tested for the presence of ATP.

As previously described, one aspect of the invention is a test system for ATP detection with sensitivity to detect food residue ATP at the level required of allergen tests. Such a screening test could be used alone or in combination with a confirmatory specific allergen detection test, such as an antibody-binding assay, for detection of specific allergens such as peanut allergen. Food residue related ATP that may be detected using this method include, without limitation, peanut, soy nut, peanut butter, almond, walnut, pecan, egg white, whole egg, pasteurized whole milk, whole wheat flour, white flour, raw clams, raw shrimp, salmon, sunflower seeds, sesame seeds, powdered milk, soy flour and ultra high temperature milk.

Use of such an ATP detection method for allergen detection, alone or in combination with specific allergen tests, can reduce testing costs and testing time by allowing rapid, inexpensive surface screening. Such a test would also be useful in expediting remediation of suspect surfaces. After surface cleanliness has been determined with the ATP test system, confirmation of either lack of, or presence of, specific allergen can be made with a specific allergen test.

Definitions

Within this application we use the term "buffer" both in accordance with its ordinary meaning and with an additional meaning. The ordinary meaning in the art is a solution that resists change in pH when acid or alkali is added. We also use the term "buffer" to refer to solutions, such as pH 6 water, which provide little buffering in the ordinary sense and, instead, impart a desired pH to a particular reaction.

BRIEF DESCRIPTION OF THE FIGURES

FIGS. 1A and 1B are schematic views of a sampling test device. FIG. 1A shows the swab removed from the test device and FIG. 1B shows the swab in a pre-use position within the device.

FIG. 2A shows insertion of a vial into a bench-top luminometer and

FIG. 2B shows insertion of a complete test device into a hand-held luminometer.

FIG. 3 graphically shows photon counters per second as a function of time at various ATP concentrations (0.5, 0.1, 0.01, 0.001 and 0 fmol ATP).

FIG. 4 graphically shows photon counters per second as a function of time at various low ATP concentrations (0.01, 0.001 and 0 fmol ATP).

FIGS. 5A, 5B, 5C and 5D show various curve fits to predict extended RLU counts from 20 second RLU counts as follows: 5A (Power Curve Fit), 5B (Exponential Curve Fit), 5C (Linear Trend Fit) and 5D (Polynomial Curve Fit).

FIG. 6 shows sample data from a Power Curve Fit analysis using two different luminometers at zero fmol ATP and 0.005 fmol ATP.

FIG. 7 shows sample data from a Power Curve Fit analysis using two different luminometers at 0.0 fmol ATP, 0.1 fmol ATP and 1 fmol ATP.

FIG. 8 shows sample data from an Exponential Curve Fit analysis using two different luminometers at zero fmol ATP and 0.005 fmol ATP.

FIG. 9 shows sample data from an Exponential Curve Fit analysis using two different luminometers at 0.01 fmol ATP, 0.1 fmol ATP and 1 fmol ATP.

FIG. 10 shows sample data from a Linear Curve Fit analysis using two different luminometers at zero fmol ATP and 0.005 fmol ATP.

FIG. 11 shows sample data from a Linear Curve Fit analysis using two different luminometers at 0.0 fmol ATP, 0.1 fmol ATP and 1 fmol ATP.

FIG. 12 shows sample data from a Polynomial Curve Fit analysis using two different luminometers at zero fmol ATP and 0.005 fmol ATP.

FIG. 13 shows sample data from a Polynomial Curve Fit analysis using two different luminometers at 0.01 fmol ATP, 0.1 fmol ATP and 1 fmol ATP.

FIG. 14 shows sample data from an average of Exponential and Power Curve Fit analysis using two different luminometers at zero fmol ATP and 0.005 fmol ATP.

FIG. 15 shows sample data from an average of Exponential and Power Curve Fit analysis using two different luminometers at 0.01 fmol ATP, 0.1 fmol ATP and 1 fmol ATP.

DESCRIPTION OF THE INVENTION

Figure 16:
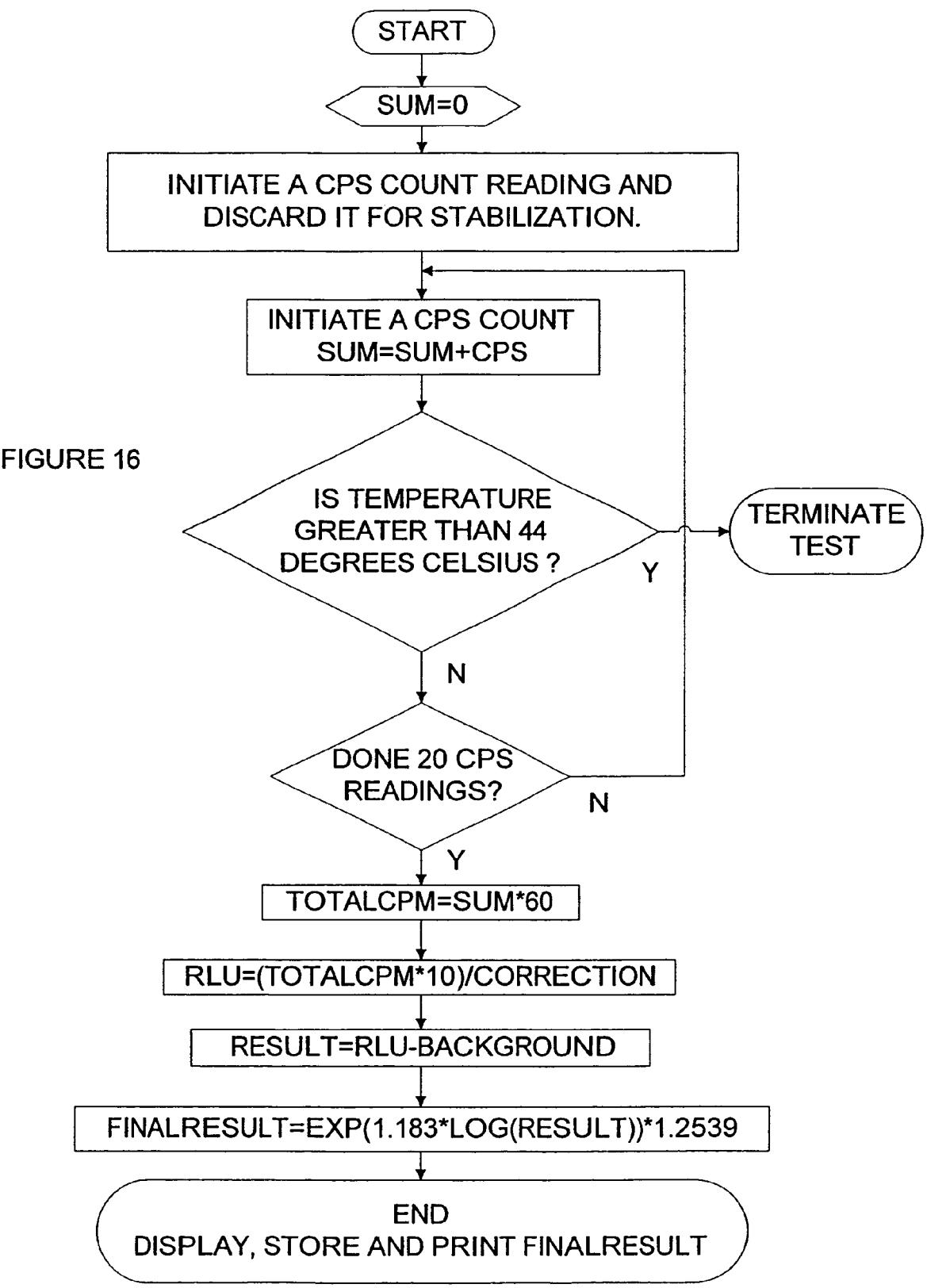
FIG. 16 is a flow chart showing an example of an accumulative algorithm to increase ATP sensitivity of a luminometer using a 20 second count to predict and extended count.

One embodiment of the invention is a method for optimizing or increasing the sensitivity of ATP detection systems. The method is useful as a technique to increase ATP sensitivity of an ATP detection test device without the added expense of increasing the concentrations of costly components such as luciferin or luciferase. In addition to increasing test costs, increasing the concentrations of luciferin and luciferase can have the undesirable result of increasing the background of the test system. Increasing the background can cause misleading results. For example, a negative sample will cause a reading unrelated to the amount of contamination detected.

In a particular embodiment the ATP detection method involves a test device with a foam tip, or other absorbent type swab or wand for sample uptake from the surface to be monitored. The swab can be pre-moistened with a wetting solution. In some embodiments the swab is pre-moistened with the same solution used elsewhere in the system, for example pre-moistened with a buffering-ATP releasing solution (BAR solution). After sample uptake (for example by absorption through swabbing a surface, pipetting onto the swab or dipping the swab into a sample) onto a swab, the swab is used to contact the sample with the various components of the device. In an embodiment, the swab first contacts a BAR solution and then contacts a luciferin/luciferase reagent composition.

In one embodiment, luciferin is highly purified beetle D-Luciferin free acid from Regis Technologies, Inc., Catalog # 360100; and r-luciferase is from PROMEGA, catalog number E-170x, specific activity $2\times10^{10}$ relative light units per mg protein (minimum specification $3.3\times10^{10}$ relative light units per mg protein). The luciferin and luciferase can be freeze dried together, for example with ATP-free bulking agents and stabilizers, and, optionally, tableted. The ratio of luciferin to BAR solution can be, for example, a ratio of about 0.07 to about 0.08 micrograms luciferin per microliter BAR solution. The ratio of luciferase to BAR solution ratio can be, for example, about 0.007 to about 0.008 micrograms luciferase per microliter BAR solution. In a specific example, 300 microliters of BAR solution was used.

It is a further aspect of this invention that the ratio of luciferase and luciferin can be changed, for example in combination with use of an optimum regression formula, to achieve optimum results. For example, the ratio of luciferase to BAR solution can be increased along with, or independently of, increasing the ratio of luciferin to BAR solution. Furthermore, it is possible, utilizing the improved methods of reading the luminescence output described herein, to reduce the ratio or amount of luciferase and/or luciferin thereby decreasing the cost per test.

In an embodiment in which ATP sensitivity is increased without increasing luciferin or luciferase concentrations, the BAR solution is a phosphate buffer that includes purified water and potassium phosphate. In a preferred embodiment, dibasic potassium phosphate is used. In these embodiments, the molarity of the buffer is less than about 10 millimolar, for example between about 0.1 and about 1.0 millimolar, for example about 0.24 millimolar. The pH of the buffer is adjusted to the range of about 6.0 to about 8.0 using, for example, sodium hydroxide or phosphoric acid, depending on the salt form used. One useful phosphate buffer, at pH 7.2+/−0.2, is available commercially and is known as Butterfield's Buffer. Another useful phosphate buffer utilizes dibasic phosphate and after combining with a detergent, such as benzalkonium chloride, for example about 0.005 percent benzalkonium chloride, has a pH of about 6.9. Other useful phosphate buffers include various mono, di and polyphosphates and their various salts for example phosphoric acid and its sodium, potassium or other salts such as monobasic sodium phosphate, dibasic sodium phosphate, tribasic sodium phosphate, diphosphoric acid and in its sodium or potassium form and other salts and polyphosphoric acid and its various salts.

Detergents can be included in the BAR solution, for example when a phosphate buffer is used as the BAR solution, to increase test sensitivity. Possible detergents or combinations of detergents are known to those skilled in the art and include nonionic detergents such as Triton X-100, Tween 20, Tween 80, Nonidet P40 and n-Undecyl Beta-D glucopyranoside; zwitterionic detergents such as n-hexadecyl-N,N-dimethyl-3-ammonio-1-propanesulfonate; and cationic detergents such as alkyltrimethylethylammonium bromides, cetyldimethylethylammonium bromide, dodecyltrimethylammonium bromide, and cetyltrimethylammonium bromide. The concentration of detergent solution varies for each type of detergent. In one embodiment of the invention a detergent, for example a quarternary amine such as benzalkonium chloride, is added to the phosphate buffer solution to improve the luminescence reaction and, therefore, test sensitivity. In a particular embodiment, the benzalkonium chloride concentration of the phosphate buffer is less than about 0.01%, for example about 0.005%.

In a particular embodiment, the BAR solution was a combination of about 10 millimolar dibasic phosphate buffer combined with about 0.005% benzalkonium chloride. In another embodiment, the BAR solution was less than about 1.0 millimolar dibasic phosphate buffer, for example about 0.1 to about 0.5 millimolar dibasic phosphate buffer. In a particular embodiment, about 0.2 to about 0.3 millimolar dibasic phosphate buffer is combined with benzalkonium chloride in a ratio of about 99.995% phosphate buffer to about 0.005% benzalkonium chloride, to a total volume of about 300 microliters.

In an example using increased luciferin and/or increased luciferase relative to BAR solution as a method of increasing test sensitivity to ATP, a BAR solution of 3.138% Trizma Base, 3.125% phosphoric acid detergent, 1.344% Tricine, 1.344% Triton X-100 (10% solution) and 0.172% benzalkonium chloride (10% solution) and deionized water was prepared. (Displacement measurements for Trizma base and tricine were used to calculate the volume of deionized water needed.) The molarity of the BAR solution as described above, is greater than about 300 millimolar. The ratio of luciferase to BAR solution was 0.2409 micrograms luciferase per microliter BAR solution and the ratio of luciferin to BAR solution was 0.481 micrograms luciferin per microliter BAR solution. The result was a 100 fold increase in assay sensitivity, as compared with a similar formulation utilizing the Charm POCKETSWAB Plus (POCKETSWAB Plus containing approximately 0.073 luciferin to BAR solution and 0.0073 luciferase to BAR solution), allowing detection of 0.05 femtomoles ATP.

An embodiment using a decrease in luciferase concentration as compared to the above example, demonstrates that by decreasing the molarity of the BAR solution ATP sensitivity may be increased. In this embodiment, BAR solution was water of about pH 6. The ratio of luciferase to BAR solution was 0.0365 micrograms per microliter (less than the 0.2409 micrograms per microliter described in the previous example) and the ratio of luciferin to BAR was about 0.07 micrograms per microliter. The result was a 100 fold increase in assay sensitivity relative to Charm PocketSwab Plus (PocketSwab Plus containing approximately 0.07 luciferin to BAR solution and 0.007 luciferase to BAR solution), allowing a maximum sensitivity of approximately 0.05 femtomoles ATP. Peanut butter was detectable with a sensitivity of 5 parts per million.

Other embodiments of this invention include generally using low molarity BAR solutions as a method of increasing test sensitivity to ATP (increasing luminesence output) without increasing luciferin/luciferase ratios relative to BAR solution. Specific embodiments for providing an increase in ATP sensitivity without relying on changes in luciferin/luciferase ratios relative to BAR solution include utilizing the following as BAR solutions: 1) phosphate buffer, for example Butterfield's Buffer (less than 1 millimolar dibasic phosphate); 2) phosphate buffer, for example Butterfield's Buffer containing a detergent, such as a quarternary amine, such as benzalkonium chloride, for example in a concentration less than 0.1%; 3) water pH of about 5.5 to pH of about 6.5; 4) water pH about 5.5 to about 6.5 with detergent such as a quarternary amine, such as benzalkonium chloride; 5) Tris-tricine buffer; 6) dibasic phosphate buffer; 7) dibasic phosphate buffer, containing a detergent, such as a quarternary amine, such as benzalkonium chloride, for example in a concentration less than 0.1% with a pH less than about pH 7.2; 8) tricine buffer, for example about 10 millimolar to about 100 millimolar tricine with or without a detergent such as quarternary amine, such as benzalkonium chloride, for example in a concentration less than 0.1%; and 9) dibasic phosphate buffer, such as Butterfields Buffer or equivalent, for example with a molarity of about 0.2 to about 0.5 with or without detergent such as benzalkonium chloride, for example in a ratio of about 99.995% phosphate buffer to about 0.005% benzalkonium chloride, with a pH of about 6.9.

In a particular embodiment, using the BAR solution described in 9 above, the pH of the BAR solution is less than about 7.2, for example about 6.9. In one example of this particular embodiment, the BAR solution is combined with a luciferin and luciferase reagent composition, said composition including other buffers, co-factors and stabilizers well known in the art. In one embodiment, approximately 0.24 millimolar dibasic potassium phosphate is used in the BAR solution and, approximately, 0.03 micrograms glycine (1.4 millimolar when combined with 300 microliter BAR solution) is used in the luciferin and luciferase reagent composition. In such an embodiment, the final reaction pH will be, for example less than about 6.9 and the molar concentration of total buffer, including phosphate and glycine will be less than about 2 millimolar.

In an embodiment the BAR solution is provided within a chamber of a test system, said chamber sealed with at least one, and generally two, puncturable membrane seals. Examples of test systems utilizing such chambers (herein sometimes referred to as niblets) include the POCKETSWAB-Plus, POCKETSWAB Ultra, POCKETH2O and ALLERGIENE. After sample contact, the swab is used to puncture the niblet membrane, or membrane seals of a series of niblets, thereby releasing, for example into a test vial, and activating the necessary reagents. Generally, the test vial is a transparent or translucent vial, which permits the passage or emission of generated luminescence, for example, in a bioluminescent assay, and, for example, permits luminescence transmission of from about 300 to 650 nanometers, which is the visible light range.

Methods and test devices for luminescence based ATP detection require readers generally known as luminometers, for example, the luminometer described in U.S. Pat. No. 6,055,050. Said luminometer may be used in combination with a system including reagents for generation of luminescence in the presence of a target sample, for example the single service ATP detection device known as the POCKETSWAB and described in U.S. Pat. No. 6,055,050 and further described in U.S. Pat. No. 5,965,453 (Test Apparatus, System and Method for the Detection of Test Samples); U.S. Pat. No. 5,985,675 (Test Device for Detection of an Analyte) and U.S. Reissue patent application Ser. No. 10/014,154; U.S. Pat. No. 6,180,395 (Reagent Chamber for Test Apparatus and Test Apparatus); all of which are incorporated herein by this reference. The luminescence reader may, for example, be in the format of the LUMINATOR-K, LUMINATOR®-T, FIREFLY® and LUM-96® readers (Luminator-K and Luminator-T are trademarks of Charm Sciences, Inc.; Luminator, Firefly and LUM-96 are registered trademarks of Charm Sciences, Inc. Lawrence, Massachusetts.) The luminescence reader may also be in the format of any luminescence reading device that detects RLU's such as by using a photodiode, or as with a photomultiplier based luminometer. In these embodiments, the test apparatus provides a user with the luminescence emission count, in RLU's, of a test sample.

In some embodiments the test result is compared with a background. A background count is, for example an RLU reading not resulting from sample ATP. One possible source of background counts is electrical noise. In certain light detection systems such as photomultiplier based systems, a source of background counts may be what is known in the art as "dark counts" resulting from, for example, thermal, chemiluminescent, or fluorescent emissions from test components. It is also possible that background counts result from outside light sources if the light detection mechanism is not contained within a perfectly light sealed environment. In well-designed and constructed equipment, such sources of background counts are relatively minimal. A more important source of background counts is residual ATP present in test reagents. In a photomultiplier based system, such residual ATP will result in RLU counts. One method for eliminating the impact of background counts is to program the reader to remove background counts from the result.

In several embodiments a background is determined for a particular instrument by running multiple tests without sample. In an example, a POCKETSWAB, for example a POCKETSWAB with BAR solution and luciferin/luciferase concentration chosen to be adequately sensitive and cost effective is not contacted with a sample and is instead contacted with only the reagents and solutions of the system and counted on a luminometer ("activated negative swab"). In one particular example 30 activated negative swabs are counted with a 5 minute cumulative count (300 RLU counts per second counts added together). The standard deviation of those 30 cumulative counts is determined and used to adjust the background reading to assure a positive test result is not caused by a high background reading. In one example, a certain number of standard deviations, from about 2 standard deviations to about 5 or more, or fractions thereof, are added to the median or average counts. For example, in one embodiment, 2.5 standard deviations are added to the median result of the multiple, for example, 30 readings. In another example, 3 standard deviations are added. The standard deviation adjustment will vary and is at least partially dependent on reagent consistency, and target test specificity and sensitivity.

In another embodiment, 30 activated negative swabs are read on multiple luminometers. The background is set relative to counts of the activated negative swabs on the multiple luminometers.

After calculation, the background can be programmed into the reader. As a sample count proceeds the reader program compares cumulative readings to the background. If the cumulative reading becomes greater than the background, then the sample is determined to contain ATP. In one embodiment, the background of the reader is set so that counts above zero indicate a positive result. In another embodiment, counts above a value other than zero indicate a positive result.

Cumulative readings can exceed background at any time up to the maximum predetermined count time, for example 5 minutes. If the maximum predetermined count time is reached, and the cumulative readings have not exceeded the background, the sample is negative. Conversely, for highly contaminated surfaces, cumulative readings can exceed background relatively quickly making it unnecessary to continue with the full 5 minute count.

In another embodiment, the luminometer, for example a luminometer described above, is optimized by adjusting the luminescence output reading and interpretation, for example by using for example a cumulative RLU/second reading, a peak RLU reading and/or an integrating RLU/second reading. These readings can be over 5 seconds or, to increase test sensitivity, over an extended period of time such as, for example, 10 seconds, 20 seconds or 30 seconds up to 5 minutes or more. This method for optimizing the luminometer can be used alone, or preferably in combination with increasing luciferin/luciferase levels and/or improved BAR solutions, as a method for increasing test sensitivity. In addition to use with photomultiplier based luminometers, or other luminescence output readers, such methods for increasing test sensitivity can be used with other types of light detectors such as photodiodes.

In some embodiments, after contacting the sample with the BAR solution to create a first admixture, the first admixture is contacted with luciferin and luciferase reagents to create a second admixture. The reaction of ATP from the sample with the luciferin/luciferase reagents generates luminescence. As previously described, the system includes a reader to detect said luminescence. Said reader detects RLU'S, generally RLU's emitted per second. Said reader can be programmed to detect RLU's over a period of time ranging from a few seconds, for example 5 seconds to several minutes, for example 5 or 10 minutes. It will be appreciated by those skilled in the art that a reading of RLU/second is common in the ATP hygiene monitoring industry. It is possible, however, to change the RLU/second to a different RLU per time reading, for example, RLU per one-half second or RLU per 2 second.

In one embodiment, desired ATP sensitivity levels are achieved through optimizing the light output reading and interpretation, for example by using a cumulative or integrated RLU/second reading or a peak RLU reading, over an extended period of time alone or in combination with increasing luciferin/luciferase levels and improving the BAR solution.

In an embodiment of the invention the reader accumulates RLU/second readings. The accumulated reading is used as a result. For example, the reader may be programmed to accumulate readings over the course of about 5 seconds to about 10 minutes or more. (The upper limit of time being limited only by background interference, the reagents and the amount of time the user can typically spend awaiting a test result.) For example, in a 5 minute count, the reader will take a count of the RLU's emitted from the sample every second generating 300 readings. The total of those 300 readings will be the test result.

Other possible embodiments include using a reader or a connected CPU programmed to: 1) take 300 readings over the course of 5 minutes. Of those 300 readings a subset is chosen, for example a subset defined by the highest 100 readings. Those 100 readings are then accumulated to provide a test result; 2) take 300 readings and determine the highest, or peak, reading. A subset of readings is chosen by reference to the peak, for example 50 readings prior and 50 readings subsequent to the peak. That subset is then used as the subset to cumulate readings; 3) integrate the counts and the result reflects the area under the integration curve; 4) take the median reading and choose a subset of readings, by reference to the median reading, to use in the result calculation; 5) determine the peak RLU/second reading and using that peak reading as the test result; 6) use a group of peak readings, for example the highest 50 readings to generate the peak reading result. The readings can be averaged, accumulated or otherwise manipulated, for example by determining the median reading, to arrive at the "peak" readings; and 7) calculate the rate of change of the RLU/second readings over a given period of time. That rate of change is used to determine the test result.

It will be appreciated that the reading time, for example a 5 minute reading, is provided by way of example only. Depending on the product test or the sensitivity desired the reading time or method can be adjusted. For example, readings can be accumulated over the course of about 5 seconds upward of about 10 minutes. The upper limit is restricted only by the need for a timely result, the reagents used and background interferences. It will be appreciated that the program for manipulating and/or interpreting the readings can be a program internal to the reader or contained in a separate system, such as a computer, to which the reader results are downloaded or otherwise accessible.

In another embodiment the rate of change of the RLU/second readings is determined over a given period of time. That rate of change is used to determine the test result, for example by a software program within the reader or a software program in a separate computer to which reader results are downloaded.

The method of reading results described herein, and the various BAR solutions, can be used with a variety of luminescence generating reagents including chemiluminescent reagents, for example dioxetane derivatives such as those available from APPLIED BIOSYSTEMS (Applied Biosystems is a registered trademark of Perkin-Elmer Corporation, Foster City, Calif.) and bioluminescent reagents, for example those available from PROMEGA. The method can also be used with luciferase from both natural and recombinant sources including heat stable luciferase. Using, for example dioxetane derivatives, compounds other than ATP can be detected and used, for example, as a marker of contamination.

As described above, we have found that extending the count time beyond 5 seconds, for example to 5 minutes, and accumulating the counts, rather than averaging the counts, provides increased sensitivity as compared to a 5 second average RLU count. However, it is also desirable to provide a more rapid result to the user. In some applications of ATP detection, time is of the essence. It may not be practical or desirable to wait one or more minutes for results. We have found that results similar to those observed in an extended cumulative count can be calculated from counts of a shorter time period, for example counting RLU's per second, for about 5 seconds to about 30 seconds, adding together the RLU's per second counts to arrive at the total RLU generated during those times, and then using one of a variety of possible formulas, to predict total counts over an extended longer time. These methods can be used with a variety of ATP detection methods for example those described heretofore and hereinafter within this application. In these embodiments, sample RLU results, after a brief period of time, for example 5 seconds, 10 seconds, 20 seconds, or 30 seconds, are used to calculate an expected result after, for example 5 minutes. In one example, a regression curve formula is used to calculate an expected 5 minute result from an actual 20 second cumulative RLU result. Examples of useful regression formulas include power curve, exponential curve, polynomial curve and linear trend formulas. Some specific embodiments include:

1. A power curve method in which $y=1.2539*x^{1.183}$ where y is the result sought (the predicted result after 5 minutes) and x is the 20 second result converted to counts per minute and corrected by reference to a standard LUMINATOR-T.

2. An exponential curve method in which $y=59597*e^{(3.3426E-05x)}$ where y is the result sought (the predicted result after 5 minutes) and x is the 20 second result converted to counts per minute and corrected by reference to a standard LUMINATOR-T.

3. A linear equation method in which $y=60594+11.261x$ where y is the result sought (the predicted result after 5 minutes) and x is the 20 second result converted to counts per minute and corrected by reference to a standard LUMINATOR-T.

4. A polynomial curve method in which $y=-13737+7.5027*x+3.9039E-05x^2$ where y is the result sought (the predicted result after 5 minutes) and x is the 20 second result converted to counts per minute and corrected by reference to a standard LUMINATOR-T In another example, results from two or more regression formulas are averaged to arrive at a result. For example, results from a given polynomial curve formula and results from a given power curve formula can be averaged to provide a final predicted 5 minute reading.

It will be appreciated that the program for manipulating, interpreting or calculating results, using one or more types of regression analysis, will be internal to the particular reader, for example luminometer or photodiode based reader, or contained in a separate system to which the particular reader results are downloaded or otherwise accessible. It will also be appreciated that there are many derivations of the above specific equations and that the above equations are provided by way of example only.

Conversion of counts per second to counts per minute can be accomplished by multiplying each 1 second count by 60. In particular embodiments the luminometer, or other reader, is adjusted by reference to a standard. For example, adjusting luminometers by reference to a control luminometer standardizes readings from one luminometer to another for a given set of reagents and a given sample. Correction factors are used to make the adjustments. Examples of corrections factor amount are between about 200 and about 300. A formula used to calculate the correction factor can be:

$$cpm*10/\text{correction factor},$$

where cpm is counts per minute calculated from a counts per second reading. The correction factor is determined by results from a particular luminometer with reference to a control luminometer.

In addition to the various luciferin-luciferase reagent combinations described herein, it is possible to use the methods and devices of this invention with other reagent systems, particularly those for measuring and detecting ATP. In various embodiments, reagents allowing regeneration of ATP, such as described by Foote et al, U.S. Pat. No. 6,043,047, issued Mar. 28, 2000 and regeneration of luciferin such as described by Kurosawa et al, EP 1 306 435 A1, published May 2, 2003, may be used.

It will be appreciated to those skilled in the art that the various herein described methods of reading and calculating a hygiene test result, such as using an extended or cumulative count alone or in conjunction with regression analysis, and thereby detecting surface residue contamination, are not limited to detection of ATP using luciferin-luciferase based luminescence detection. For example certain of these methods may be usefully applied to reading and analyzing the results from color based tests, for example color tests for detection of protein, glucose or other carbohydrates or phosphates such as those described in U.S. patent application Ser. No. 10/343,582 (Hygiene Monitoring), Jan. 31, 2003 which is incorporated herein by reference.

Other examples of tests for which the herein described method of reading and extrapolating (predicting) a hygiene test result may be used, which may not involve ATP detection or luminescence output, include those described in U.S. Pat. No. 6,551,834, Issued Apr. 22, 2003 (Detection of Contaminants Using Self-Contained Devices Employing Target Material Binding Dyes); U.S. Pat. No. 6,387,650, Issued May 14, 2002 (Method and Composition for Detecting Bacterial Contamination in Food Products); U.S. Pat. No. 6,043,047, issued Mar. 28, 2000 (Sample-Collecting and Assay Device For Use In the Detection of Biological Material) and European Patent 0 695 363 B1, Sep. 17, 1997 (Detection of Biological Material).

DESCRIPTION OF THE FIGURES

FIGS. 1A and 1B illustrate the invention in the format of the POCKETSWAB-PLUS type device (the format of the POCKETSWAB Ultra/H2O Plus/ALLERGIENE (ALLERGIENE is a trademark of Charm Sciences, Inc. Lawrence, MA) test device is basically the same with only a change in the BAR solution as described herein). FIG. 1A is a schematic view of the swab removed form the test device and FIG. 1B is a schematic view of the test device containing the swab. In use of the swab type device of the invention, the swab 1 is removed from the body 3, by gripping the swab handle 2, and a 4"×4" surface, for example a food contact surface, is swabbed using the pre-moistened swab 1. (The swab 1 is provided pre-moistened, for example, with the same BAR solution provided in the niblet 5.) Alternatively the swab 1 can be dipped into the sample or the sample can be pipetted onto the swab 1. The swab 1 is then reinserted into the body 3 and screwed longitudinally through the covering 9 of the microtube test unit 4 and through the covering 10 of the niblet 5 and into bottom of the microtube test unit 4. In an embodiment, the liquid reagent niblet 5 contains, a BAR solution such as those described herein. The liquid within the BAR solution niblet 5 dissolves the reagent 7 containing luciferin-luciferase. The resulting luminescence is read using a luminometer.

FIGS. 2A and 2B illustrates insertion of the POCKETSWAB PLUS TEST device, or POCKETSWAB Ultra/H2O Plus/ALLERGIENE Test Device into a Charm LUMINATOR-K11) and Charm LUMINATOR-T12). Results are read using, for example, one of the methods described herein, and a result is provided on the display 13, 14. The result, is provided, for example numerically or alternatively as a positive or negative.

FIG. 3 is a graphical representation of data generated using various concentrations of ATP represented in the graph legend as femtomoles (fmol) ATP. BAR solution contained 99.995% Butterfield's Buffer with 0.005% benzalkonium chloride. Light output was read using a LUMINATOR-T. Three hundred accumulated RLU/second readings (5 minutes total) were used to generate each line on the graph. This graph illustrates that a cumulative reading over an extended period of time, as opposed to an average or a reading of the amplitude (peak), allows the user to distinguish lower levels of ATP.

FIG. 4 is a graphical representation of a subset of data from FIG. 3. The scale of the graph, from 0 to 1000 RLU's, further illustrates assay sensitivity relative to relatively low levels (0.01 fmol and 0.001 fmol) of ATP.

FIGS. 5A, 5B, 5C, and 5D are graphical representations of data generated by four different types of regression analysis: power curve fit—FIG. 5A; linear trend fit—FIG. 5B; exponential curve fit—FIG. 5C; and polynomial curve fit—FIG. 5D.

The results shown in FIGS. 6 and 7 (power curve), 8 and 9 (exponential curve), 10 and 11 (linear trendline), 12 and 13 (polynomial curve), and 14 and 15 (average of exponential and power curves) were generated using two different LUMINATOR-T analyzers. Results were generated using five different concentrations of ATP (including zero). Correction factors were used to standardize results from both analyzers to within 5% of a control unit. The average of the corrected values was used. Average of multiple results for 20 second cumulative counts were compared to the average of multiple results from 300 second cumulative counts each for two separate LUMINATOR-T units. For each of FIGS. 6 through 15, column 1 (Col 1) shows the result of 20 cps (counts per second) counts summed at 20 seconds. For each of FIGS. 6 through 15, column 2 (Col 2) shows the result of the conversion of cps to counts per minute (cpm) by multiplying Col 1 times 60. For each of FIGS. 6 through 15, column 3 (Col 3) shows the corrected value which is calculated by multiplying by 10 the Col 2 results and dividing the product by the correction factor (CF) for the particular LUMINATOR-T used. For each of FIGS. 6 through 15, column 4 (Col 4) shows the actual relative light unit (RLU) results generated by summing 300 cps counts after 300 seconds.

The average results were subjected to various types of regression analysis to determine a best fit formula for each type of regression analysis. Column 5 (Col 5) in FIGS. 6 and 7 (Power Curve Analysis) used the regression formula $y=1.2539*x^{(1.183)}$, to use 20 second results to calculate 300 second results: R=0.99914. Column 5 (Col 5) in FIGS. 8 and 9 (Exponential Curve Analysis) used the regression formula y=59597*e^(3.3426E−05x), to use 20 second results to calculate 300 second results: R=0.99357. Column 5 (Col 5) in FIGS. 10 and 11 (Linear Curve Analysis) used the regression formula y=−60594+11.261x, to use 20 second results to calculate 300 second results: R=0.99805. Column 5 (Col 5) in FIGS. 12 and 13 (Polynomial Curve Analysis) used the regression formula y=−13737+7.5027*x+3.9039E−05x^2: to use 20 second results to calculate 300 second results: R=0.99909. Column 5 (Col 5) in FIGS. 14 and 15 (Average of Exponential and Power Curves) used the regression formula y=[(59597*e^(3.3426E−05x))+(1.2539*x^(1.183))]/2 to use 20 second results to calculate 300 second results. The results show that one or more of the best fit formulas, alone or in combination, have R values sufficiently close to 1.0 to be able to accurately predict 5 minute cumulative results from actual 20 second cumulative results. Column 6 (Col 6) shows the percentage change from actual (Col 4) of the regression formula predicted 300 second results (Col 5).

It will be appreciated by those skilled in the art that 20 seconds and 5 minutes are representative time frames and are not provided as limitations on the scope of the invention.

FIG. 16 is a flow chart showing an example of an accumulative algorithm to increase ATP sensitivity of the Charm Luminometer. The flow chart demonstrates obtaining a 20 second result and using that 20 second result to compute a final result (predicted 5 minute result). Terms used in the flow chart include:

1) Correction—a value determined by a calibration technician to slope the result to match a pre-calibrated standard Luminometer.

2) Background—a value determined by a calibration technician to set a threshold at which detection of a contaminant is obtained and begins to show a positive result.

3) RLU—Relative Light Units.

4) CPS—Counts Per Second.

5) Total CPM—total of CPS counts multiplied by 60 to predict Total Counts per minute.

6) Exp(x)—a Math library function which returns the exponential value of x.

7) Log(x)—a Math Library function which returns the natural logarithm of x (base e=2.718282).

The algorithm can be within a program internal to the luminometer or in an external component to which data is transferred, such as an associated central processing unit. The particular algorthim/flowchart describes a method for reading luminescent test results that includes a series of count per second readings. The initial count is disregarded to avoid the possible impact of an initial aberrant result. An internal temperature check is included to avoid incorrect results caused by excessive luminometer temperatures. Twenty CPS's are determined and summed. The total sum of the twenty CPS's is then multiplied by 60 to arrive at the total CPM. The RLU result is determined by multiplying the total CPM by a factor of 10 and dividing by the Correction. That corrected number is reduced by the Background to arrive at the Result. That Result is then used to extrapolate a predicted final result after an extended count, in this example using the power curve formula described.

EXAMPLES

Example 1

BAR solution containing 99.995% modified Butterfield's Buffer (made with dibasic rather than monobasic phosphate) with 0.005% benzalkonium chloride was prepared as follows:

A. Prepare 1 L of 0.195 M dibasic potassium phosphate as follows:
  1. Add 34 g dibasic potassium phosphate ($K_2HPO_4$; FW=174.2) to 500 mL ultra-pure water in a 1 liter Erlenmeyer flask. Mix until fully dissolved.
  2. Adjust pH to 7.20±0.02 with phosphoric acid.
  3. Bring volume to 1 L with ultra-pure water. Mix for 5 minutes.
B. Prepare 22 L of BAR solution (0.24 mM dibasic potassium phosphate) as follows:
  1. Add 27.5 mL of 0.195 M dibasic potassium phosphate to carboy with mark at 22 L.
  2. Bring volume to 22 L with ultra-pure water. Mix for 5 minutes.
  3. Dispense 3500 mL of BAR solution into six x 4 L NALGENE (Nalgene is a registered trademark of Nalge Nunce International Corporation Rochester, N.Y.)
C. Autoclave the bottles of BAR solution for 90 minutes at 121° C.
D. After autoclaving add 350 μL of 50% benzalkonium chloride to each bottle of BAR solution once the solution has cooled to room temperature. Shake well for 30 seconds to mix.

The above described BAR solution can be used with luciferin-luciferase reagents to detect ATP. In one example luciferin-luciferase were produced using highly purified beetle D-Luciferin free acid from Regis Technologies, Inc., Catalog # 360100; and r-luciferase was from PROMEGA (Promega is a registered trademark of Promega Corporation, Madison, Wisconsisn), catalog number E-170x, specific activity $2 \times 10^{10}$ relative light units per mg protein (minimum specification $3.3 \times 10^{10}$ relative light units per mg protein). The luciferin and luciferase were freeze dried together with magnesium acetate and ATP-free bulking and stabilizing agents such as lactose, BSA, glycine (1.4 millimolar glycine when combined with 300 microliter BAR solution), Ethylenediaminetetraacetic Acid (EDTA), dithiothreitol (DTT), and stabilizers such as lactose, and tableted after addition of AVICEL and magnesium stearate. The ratio of luciferin to BAR solution was about 0.073 micrograms luciferin per microliter BAR solution. The ratio of luciferase to BAR solution ratio was about 0.0073 micrograms luciferase per microliter buffer.

Example 2

For testing, 300 μL of BAR solution was used (various compositions described below) and either luciferin-luciferase liquid solution, with magnesium co-factor or without magnesium cofactor. Tabletted luciferin-luciferase (which contains additional stabilizers and magnesium cofactor) was also tested for comparison. In either case, the amount of luciferin per test was 23 μg, and the amount of luciferase was 2.3 μg. Luciferin/Luciferase tablet includes co-factor, stabilizers and bulking agents including: magnesium acetate, lactose, BSA, glycine, EDTA, DTT, lactose, AVICEL (AVICEL is a registered trademark of FMC Corporation, Philadelphia, Pa.) and magnesium stearate.

Luciferin/Luciferase liquid includes only luciferin and luciferase or alternatively as indicated luciferin and luciferase and magnesium. LUM-T background was set to 100 ("off") in order to see differences in uncorrected background values.

TABLE 1

| Niblet Solution Composition | Luciferin-Luciferase | Negative RLU Avg | 0.01 fmol ATP RLU Avg | Pos/Neg Ratio |
|---|---|---|---|---|
| Control (BB 99.995% + BC 0.005%) | tablet | 55746 | 190453 | 3.42 |
| Sterile water | tablet | 57571 | 98742 | 1.72 |
| BB alone (no BC) | tablet | 47199 | 142736 | 3.02 |
| 260 mM Tris base/75 mM Tricine; pH 7.8 | tablet | 48869 | 66665 | 1.36 |
| 20 mM Tris base/ 5 mM Tricine; pH 7.8 | tablet | 75869 | 151421 | 2.00 |
| Control (BB 99,995% + BC 0.005%) | liquid | 37596 | 40595 | 1.08 |
| Sterile water | liquid | 33300 | 32186 | 0.97 |
| Control (BB 99.995% + BC 0.005%) | Liquid + Mg | 53230 | 169660 | 3.19 |

BB = Butterfield's Buffer prepared with dibasic potassium phosphate
BC = benzalkonium chloride
Note: 260 mM Tris base/75 mM tricine, pH 7.8 is used in the niblet solution for the "standard" PocketSwab Plus. The above results show maximum sensitivity using a BAR solution of BB + BC as compared with other possible BAR solutions.

Example 3

An embodiment of the invention involves detection of bacterial contamination in water, for example food production water, rinse water or wet surfaces from cleaned equipment. In this embodiment a sample swab is dipped in sample water and swirled for approximately 5 seconds. After removal from the water sample, the swab is contacted with BAR solution, for example BAR solution containing 99.995% dibasic phosphate buffer and 0.005% benzalkonium chloride. The phosphate buffer has molarity in the range of about 0.1 millimolar to about 0.5 millimolar. After adding sample to the BAR solution the mixture is contacted with the luciferin/luciferase reagents for example the tablet described with reference to Example 1. Luminescence results are determined on a standard luminometer, for example a LUMINATOR-T or FIREFLY, utilizing a 20 second cumulative count and Power Curve generated result.

Examples 4–7

NOTE: The following examples 4–7 and related tables show detection levels for common food residues, for example 5 ppm peanut butter. Generally, the allergenic component of the food, such as peanut butter, is a protein. As a result, detection levels may refer to peanut butter protein levels rather than peanut butter levels. If peanut butter is detected at 5 ppm and peanut butter is, generally, about 22% protein then peanut butter protein can be detectable at 5 ppm×0.22, or approximately 1.1 ppm protein.

Example 4

Table 2 shows results using a BAR solution of 99.995% dibasic phosphate buffer and 0.005% benzalkonium chloride to test various potentially allergenic matrices (unsalted cocktail peanuts, peanut butter, pasteurized whole milk, raw egg white, raw whole egg, all-purpose flour) at a variety of concentrations. A 5000 ppm stock solution of each food was prepared in sterile water, then diluted serially in sterile water. Results were generated on a luminometer utilizing a 30 second cumulative RLU count and a background subtract of 15000. For testing, a 20 microliter sample was added directly to a swab. A LUMINATOR-K was used.

Luciferin-luciferase tablet containing highly purified beetle D-Luciferin free acid from Regis Technolgies, Inc., Catalog # 360100; and r-luciferase from PROMEGA, catalog number E-170x, specific activity $2 \times 10^{10}$ relative light units per mg protein (minimum specification $3.3 \times 10^{10}$ relative light units per mg protein). The luciferin and luciferase were freeze dried together, with ATP-free bulking agents and stabilizers, such as described in Example 1, and tableted. The ratio of luciferin to BAR solution ratio was about 0.073 micrograms luciferin per microliter BAR solution. The ratio of luciferase to BAR solution ratio was about 0.0073 micrograms luciferase per microliter buffer. The results show ATP detection at levels at which a positive result can be used to determine, for example, that peanut butter may be present at above 5 ppm.

TABLE 2

| Allergen/Source | | RLU Cumulative | % Positive |
|---|---|---|---|
| Blank (negative control) | | 0 | 0% |
| Peanut | | | |
| Unsalted cocktail peanuts (25% protein) | 5000 ppm | 711557 | 100% |
| | 500 ppm | 65217 | 100% |
| | 50 ppm | 8247 | 100% |
| | 25 ppm | 6630 | 100% |
| | 5 ppm | 0 | 0% |
| Peanut Butter | | | |
| Peanut butter (22% protein) | 5000 ppm | 957200 | 100% |
| | 500 ppm | 101881 | 100% |
| | 50 ppm | 7851 | 100% |
| | 25 ppm | 7072 | 100% |
| | 5 ppm | 1850 | 33% |
| Milk | | | |
| Pasteurized whole milk (~2.7% casein) | 18500 ppm | 2447813 | 100% |
| | 1850 ppm | 284021 | 100% |
| | 185 ppm | 19942 | 100% |
| | 37 ppm | 1773 | 50% |
| Egg White | | | |
| Raw egg white (~10% protein) | 50000 ppm | 20263 | 100% |
| | 25000 ppm | 11270 | 100% |
| | 10000 ppm | 768 | 100% |
| | 5000 ppm | 2519 | 50% |
| Raw whole egg (~6.7% egg white protein) | 5000 ppm | 72812 | 100% |
| | 500 ppm | 16578 | 100% |
| | 250 ppm | 4939 | 100% |
| | 50 ppm | 0 | 0% |
| Flour | | | |
| All-purpose flour (~10% protein) | 5000 ppm | 266208 | 100% |
| | 500 ppm | 34620 | 100% |
| | 250 ppm | 34188 | 100% |
| | 100 ppm | 1780 | 100% |
| | 50 ppm | 0 | 0% |

Example 5

Table 3 shows results using a BAR solution of 99.995% dibasic phosphate buffer and 0.005% benzalkonium chloride with luciferin/luciferase tablet described with reference to Example 4 and Example 1, to test the same allergenic matrices as Example 4. A 5000 ppm stock solution of each food was prepared in sterile water, then diluted serially in sterile water. A 5 second average RLU (non-cumulative in which five RLU counts per second over five seconds are averaged) count and a background subtract of 2600 were used. For testing, a 20 microliter sample was added directly to a swab. A LUMINATOR-K was used. Sensitivity decreased as compared to results shown in Example 4.

TABLE 3

| Allergen/Source | | RLU | % Positive |
|---|---|---|---|
| Blank (negative control) | | 0 | 0% |
| Peanut | | | |
| Unsalted cocktail peanuts (25% protein) | 5000 ppm | 16575 | 100% |
| | 500 ppm | 679 | 50% |
| | 50 ppm | 0 | 0% |
| | 25 ppm | 0 | 0% |
| | 5 ppm | 0 | 0% |
| Peanut Butter | | | |
| Peanut butter (22% protein) | 5000 ppm | 22264 | 100% |
| | 500 ppm | 1000 | 50% |
| | 50 ppm | 0 | 0% |
| | 25 ppm | 0 | 0% |
| | 5 ppm | 0 | 0% |
| Milk | | | |
| Pasteurized whole milk (~2.7% casein) | 18500 ppm | 62521 | 100% |
| | 1850 ppm | 5687 | 100% |
| | 185 ppm | 0 | 0% |
| | 37 ppm | 0 | 0% |
| Egg White | | | |
| Raw egg white (~10% protein) | 50000 ppm | 0 | 0% |
| | 25000 ppm | 0 | 0% |
| | 10000 ppm | 0 | 0% |
| | 5000 ppm | 0 | 0% |
| Whole Egg | | | |
| Raw whole egg (~6.7% egg white protein) | 5000 ppm | 0 | 0% |
| | 500 ppm | 0 | 0% |
| | 250 ppm | 0 | 0% |
| | 50 ppm | 0 | 0% |
| Flour | | | |
| All-purpose flour (~10% protein) | 5000 ppm | 4663 | 100% |
| | 500 ppm | 0 | 0% |
| | 250 ppm | 0 | 0% |
| | 100 ppm | 0 | 0% |
| | 50 ppm | 0 | 0% |

Example 6

Table 4 shows results using BAR solution of 260 mM Tris base/75 mM tricine, pH 7.8 (as previously used in the POCKETSWAB-PLUS test). Luciferin-luciferase tablet described with reference to Example 4 and Example 1 were used. The same allergenic matrices were tested as in Example 4. A 5000 ppm stock solution of each food was prepared in sterile water, then diluted serially in sterile water. Results were generated on a luminometer utilizing a 5 second average RLU (non-cumulative in which five RLU counts per second over five seconds are averaged) count and a background subtract of 2600. For testing, a 20 microliter sample was added directly to a swab. A LUMINATOR-K was used. Results show decreased sensitivity as compared with results in both Example 4 and Example 5.

TABLE 4

| Allergen/Source | | RLU | % Positive |
|---|---|---|---|
| Blank (negative control) | | 0 | 0% |
| Peanut | | | |
| Unsalted cocktail peanuts (25% protein) | 5000 ppm | 1916 | 100% |
| | 500 ppm | 0 | 0% |
| | 50 ppm | 0 | 0% |
| | 25 ppm | 0 | 0% |
| | 5 ppm | 0 | 0% |
| Peanut Butter | | | |
| Peanut butter (22% protein) | 5000 ppm | 4399 | 100% |
| | 500 ppm | 0 | 0% |
| | 50 ppm | 0 | 0% |
| | 25 ppm | 0 | 0% |
| | 5 ppm | 0 | 0% |
| Milk | | | |
| Pasteurized whole milk (~2.7% casein) | 18500 ppm | 18473 | 100% |
| | 1850 ppm | 2276 | 100% |
| | 185 ppm | 0 | 0% |
| | 37 ppm | 0 | 0% |
| Egg White | | | |
| Raw egg white (~10% protein) | 50000 ppm | 0 | 0% |
| | 25000 ppm | 0 | 0% |
| | 10000 ppm | 0 | 0% |
| | 5000 ppm | 0 | 0% |
| Whole Egg | | | |
| Raw whole egg (~6.7% egg white protein) | 5000 ppm | 0 | 0% |
| | 500 ppm | 0 | 0% |
| | 250 ppm | 0 | 0% |
| | 50 ppm | 0 | 0% |
| Flour | | | |
| All-purpose flour (~10% protein) | 5000 ppm | 0 | 0% |
| | 500 ppm | 0 | 0% |
| | 250 ppm | 0 | 0% |
| | 100 ppm | 0 | 0% |
| | 50 ppm | 0 | 0% |

Example 7

Table 5 shows results using a BAR solution of 99.995% dibasic phosphate buffer and 0.005% benzalkonium chloride with luciferin/luciferase tablet described with reference to Example 4 and Example 1, to test various concentrations of potentially allergenic matrices. A 5000 ppm stock solution of each food was prepared in sterile water, then diluted serially in sterile water. A 5 minute cumulative count was used. Background subtract of 100,000 was used. A LUMINATOR-K was used. Increased sensitivity, as compared with results from the next most sensitive combination (results in Example 4) was observed.

Further experiments, using a 10 minute cumulative count, increased sensitivity to egg white to 5 ppm (approximate egg white protein equivalent of 0.5 ppm). It is expected that sensitivity to other matrices may also be increased using such an extended cumulative count.

TABLE 5

| Food | Concentration | RLU Average | % Positive | Allergen Test Manufacturer Claims |
|---|---|---|---|---|
| Peanut butter (22% protein) | 5 ppm | 747242 | 100% | <0.1 to 1 ppm |
| | 0.5 ppm | 83137 | 100% | peanut protein |
| | 0.25 ppm | 60753 | 100% | (0.5 to 3 hr assay time) |
| | 0.1 ppm | 59232 | 67% | |
| | 0.05 ppm | 5188 | 33% | |
| Soy nuts (36.7% protein) | 50 ppm | 199083 | 100% | 70 to <5000 ppm |
| | 5 ppm | 61132 | 100% | soy protein |
| | 0.5 ppm | 9414 | 100% | (30 min assay time) |
| | 0.05 ppm | 0 | 0% | |
| Almond (20% protein) | 50 ppm | 217604 | 100% | 1.7 to 5 ppm |
| | 5 ppm | 71092 | 100% | almond |
| | 0.5 ppm | 4396 | 50% | (30 min assay time) |
| Walnut (16.7% protein) | 50 ppm | 182168 | 100% | unknown |
| | 5 ppm | 51090 | 100% | |
| | 0.5 ppm | 225 | 50% | |
| Pecan (10% protein) | 50 ppm | 76873 | 100% | unknown |
| | 5 ppm | 10257 | 100% | |
| | 0.5 ppm | 0 | 0% | |
| Egg white (10% protein) | 5000 ppm | 224516 | 100% | 1 to 5 ppm egg |
| | 500 ppm | 40575 | 100% | white protein |
| | 100 ppm | 33374 | 100% | (0.5 to 1.5 hr assay time) |
| | 50 ppm | 7860 | 67% | |
| Whole egg (6.7% protein) | 500 ppm | 41404 | 100% | 1 to 5 ppm egg |
| | 50 ppm | 40977 | 100% | white protein |
| | 5 ppm | 6809 | 67% | (0.5 to 1.5 hr assay time) |
| | 0.5 ppm | 187 | 33% | |
| Whole milk, pasteurized (2.7% casein) | 100 ppm | 223233 | 100% | 5 ppm |
| | 10 ppm | 105121 | 100% | milk protein |
| | 1 ppm | 29771 | 67% | (0.5 to 2 hr assay time) |
| Whole wheat flour (13.3% protein) | 100 ppm | 440020 | 100% | <2 to 8 ppm |
| | 10 ppm | 77042 | 100% | wheat proteins |
| | 1 ppm | 26010 | 100% | (0.5 to 2 hr assay time) |
| | 0.1 ppm | 32217 | 67% | |
| All-purpose white flour (10% protein) | 10 ppm | 82308 | 100% | <2 to 8 ppm |
| | 1 ppm | 29483 | 100% | wheat proteins |
| | 0.1 ppm | 0 | 0% | (0.5 to 2 hr assay time) |
| Clams, raw (12.8% protein) | 50 ppm | 130018 | 100% | unknown |
| | 25 ppm | 55383 | 100% | |
| | 10 ppm | 28197 | 40% | |
| | 5 ppm | 0 | 0% | |
| Shrimp, raw (20.3% protein) | 50 ppm | 129186 | 100% | unknown |
| | 25 ppm | 82211 | 100% | |
| | 10 ppm | 39574 | 80% | |
| | 5 ppm | 1613 | 33% | |
| Atlantic salmon, raw (19.9% protein) | 50 ppm | 48824 | 100% | unknown |
| | 25 ppm | 45425 | 100% | |
| | 10 ppm | 8237 | 60% | |
| | 5 ppm | 0 | 0% | |
| Soybeans (36.5% protein) | 50 ppm | 346842 | 100% | 70 to <5000 ppm |
| | 5 ppm | 30648 | 100% | soy protein |
| | 0.5 ppm | 3878 | 50% | (30 min assay time) |
| Sunflower seeds (20% protein) | 5 ppm | 93950 | 100% | unknown |
| | 0.5 ppm | 42704 | 100% | |
| | 0.05 ppm | 33843 | 40% | |
| Sesame seeds (17.7% protein) | 500 ppm | 508324 | 100% | 1 ppm sesame |
| | 50 ppm | 38680 | 100% | seed protein |
| | 25 ppm | 8551 | 60% | (assay time unknown) |
| Whole milk, powdered (19.7% casein) | 50 ppm | 399603 | 100% | 5 ppm |
| | 5 ppm | 50471 | 100% | milk protein |
| | 0.5 ppm | 16748 | 40% | (0.5 to 2 hr assay time) |
| Soy flour (52% protein) | 50 ppm | 399366 | 100% | 70 to <5000 ppm |
| | 5 ppm | 95755 | 100% | soy protein |
| | 0.5 ppm | 31848 | 60% | (30 min assay time) |
| Whole milk, UHT (2.7% casein)* | 1000 ppm | 32680 | 100% | 5 ppm |
| | 500 ppm | 30557 | 100% | milk protein |
| | 250 ppm | 10541 | 50% | (0.5 to 2 hr assay time) |
| | 100 ppm | 2354 | 20% | |

Example 8

Tables 6, 7, 8, and 9 show results using using a BAR solution of 99.995% dibasic phosphate buffer and 0.005% benzalkonium chloride with luciferin/luciferase tablet described with reference to Example 4 and Example 1, to test various concentrations of ATP (Table 6) Whole Egg (Table 7), Peanut Butter (Table 8) and Egg White (Table 9). RLU counts were read every second for 300 seconds and totaled. Background subtract of 100,000 was used. Results in tables 6, 7, 8 and 9 show multiple RLU readings which were averaged to arrive at particular results. These results are also summarized in particular examples in Example 7 (Table 5). A LUMINATOR-K was used.

TABLE 6

| ATP Concentration (fmol/20 uL sample) | RLU Readings | % Positive |
|---|---|---|
| 0.5 | 4196324 | 100% |
|  | 6406563 |  |
|  | 5501847 |  |
|  | Avg: 5368245 |  |
| 0.1 | 4408690 | 100% |
|  | 2138919 |  |
|  | 2345606 |  |
|  | Avg: 2964405 |  |
| 0.01 | 213632 | 100% |
|  | 250782 |  |
|  | 195101 |  |
|  | Avg: 219838 |  |
| 0.001 | 99087 | 100% |
|  | 37798 |  |
|  | 40974 |  |
|  | Avg: 59286 |  |
| 0% | 0 | 0% |
|  | 0 |  |
|  | 0 |  |
|  | Avg: 0 |  |

TABLE 7

| Whole Egg Concentration (ppm) | RLU Readings | % Positive |
|---|---|---|
| 500 | 31407 | 100% |
|  | 11446 |  |
|  | 81360 |  |
|  | Avg: 41404 |  |
| 50 | 2715 | 100% |
|  | 100510 |  |
|  | 19707 |  |
|  | Avg: 40977 |  |
| 5 | 18516 | 67% |
|  | 1911 |  |
|  | 0 |  |
|  | Avg: 6809 |  |
| 0.5 | 562 | 33% |
|  | 0 |  |
|  | 0 |  |
|  | Avg: 187 |  |
| 0 | 0 | 0% |
|  | 0 |  |
|  | 0 |  |
|  | Avg: 0 |  |

TABLE 8

| Peanut Butter Concentration (ppm) | RLU Readings | % Positive |
|---|---|---|
| 5 | 889650 | 100% |
|  | 628410 |  |
|  | 723666 |  |
|  | Avg: 747242 |  |
| 0.5 | 135814 | 100% |
|  | 54646 |  |
|  | 58950 |  |
|  | Avg: 83137 |  |
| 0.25 | 3473 | 100% |
|  | 42586 |  |
|  | 136200 |  |
|  | Avg: 60753 |  |
| 0.1 | 116374 | 67% |
|  | 61321 |  |
|  | 0 |  |
|  | Avg: 59232 |  |
| 0.05 | 0 | 33% |
|  | 0 |  |
|  | 15564 |  |
|  | Avg: 5188 |  |
| 0 | 0 | 0% |
|  | 0 |  |
|  | 0 |  |
|  | Avg: 0 |  |

TABLE 9

| Egg White Concentration (ppm) | RLU Readings | % Positive |
|---|---|---|
| 5000 (500 ppm protein) | 147025 | 100% |
|  | 302007 |  |
|  | Avg: 224516 |  |
| 500 (50 ppm protein) | 47696 | 100% |
|  | 35638 |  |
|  | 38391 |  |
|  | Avg: 40575 |  |
| 100 (10 ppm protein) | 29355 | 67% |
|  | 15956 |  |
|  | 54812 |  |
|  | Avg: 33374 |  |
| 50 (5 ppm protein) | 12769 | 67% |
|  | 0 |  |
|  | 10810 |  |
|  | Avg: 7860 |  |
| 0 | 0 | 0% |
|  | 0 |  |
|  | 0 |  |
|  | Avg: 0 |  |

Example 9

Tables 10–13 show a comparison of RLU results using three different BAR solutions (referred to as BAR A, BAR B and BAR C). In addition, luciferin/luciferase tablet described with reference to Example 4 and Example 1. BAR A solution (original formulation from PocketSwab Plus swabs) contained 3.138% Trizma Base, 3.125% phosphoric acid detergent, 1.344% Tricine, 1.344% Triton X-100 (10% solution) and 0.172% benzalkonium chloride (10% solution) and deionized water. Displacement measurements for Trizma base and tricine were used to calculate the volume of deionized water needed. BAR B solution contained Butterfield's Buffer made with dibasic phosphate (less than about 1 millimolar). BAR C solution contained 99.995% Butterfield's Buffer made with dibasic phosphate (less than about 1 millimolar) with 0.005% benzalkonium chloride.

Table 10 shows the average RLU results from a comparison of BAR A, BAR B and BAR C using the luciferin/luciferase tablet described with reference to Example 4 and Example 1 and varying concentrations of ATP from 0 to 180 femtomoles. Both the LUMT and FIREFLY luminometers were used with background subtract. Results show increased sensitivity by decreasing the molarity of the BAR solution, using only Butterfield's Buffer (low molarity phosphate buffer) made with dibasic phosphate. BAR C shows the best sensitivity when 0.005% benzalkonium chloride is added to Butterfield's Buffer made with dibasic phosphate.

TABLE 10

|  | LUMT | FIREFLY |  |
|---|---|---|---|
| BAR-A | 81,900 | 21,013 | 180 fmoles ATP |
| BAR-B | 129,933 | 34,459 |  |
| BAR-C | 218,366 | 65,112 |  |
| BAR-A | 8,368 | 752 | 18 fmoles ATP |
| BAR-B | 9,748 | 1,066 |  |
| BAR-C | 16,636 | 2,665 |  |
| BAR-A | 0 | 0 | 1.8 fmoles ATP |
| BAR-B | 0 | 0 |  |
| BAR-C | 2,869 | 0 |  |
| BAR-A | 0 | 0 | 0 fmoles ATP |
| BAR-B | 0 | 0 |  |
| BAR-C | 0 | 0 |  |

Table 11 shows comparative RLU results using BAR A, BAR B and BAR C and sample uptake by swabbing a surface contaminated with a variety of food residues. The results again show overall increased sensitivity using BAR C. Surface squares tested with finished unit on LUMINATOR-T with background subtract.

TABLE 11

| Solution | Chicken | Juice | Egg | milk |
|---|---|---|---|---|
| BAR-A | 130582 | 3800 | 9902 | 4777 |
| BAR-C | 169327 | 89186 | 60948 | 51338 |
| BAR-B | 209985 | 24938 | 23509 | 29156 |

Table 12 shows the average RLU results from a comparison of BAR A, BAR B and BAR C using the luciferin/luciferase tablet described with reference to Example 4 and Example 1 and varying concentrations (dilutions) of a variety of bacteria by pipetting 10 microliters onto each swab. LUMINATOR-T was used with background subtract.

TABLE 12

Bacterial Study done by pipetting 10 ul onto each swab system

| Solution | C. freundii | S. cerevisiae | P. agglomerans | P. fluorescens |  |
|---|---|---|---|---|---|
| BAR-A | 10315 | 36163 | 30633 | 5931 | Diln 10-2 |
| BAR-C | 15280 | 582814 | 45942 | 5525 |  |
| BAR-B | 12603 | 56975 | 18555 | 21306 |  |
| BAR-A | 0 | 2509 | 5180 | 0 | Diln 10-3 |
| BAR-C | 115 | 53092 | 1953 | 513 |  |
| BAR-B | 0 | 3828 | 14375 | 0 |  |
| BAR-A | 0 | 0 | 8646 | 0 | Diln 10-4 |
| BAR-C | 0 | 1556 | 275 | 0 |  |
| BAR-B | 0 | 3868 | 3880 | 0 |  |

Tables 13A, 13B, 13C, 13D, 13E, 13F show results from a variety of stability, sensitivity and test background experiments.

TABLE 13A

The results show increased count stability between 1 and 2 minutes after test initiation using a 180 femtomole concentration of ATP and BAR A versus BAR C. Results shown are from the same test recounted and show that BAR C, in addition to increased sensitivity, provided increased test result stability. LUMINATOR-T with background subtract.

180 fmoles

|  | Initial | 1 min | % change | 2 min | % change |
|---|---|---|---|---|---|
| BAR-A | 111,065 | 94,115 | −15% | 70,426 | −37% |
| BAR-C | 205,833 | 205,638 | −0.10% | 196,642 | −4% |

TABLE 13B

The results show a comparison of results using BAR B and BAR C testing a 60 femtomole concentration of ATP. LUMINATOR-K was used with no background subtract.

|  | Zero | 60 fmoles ATP |
|---|---|---|
| BAR-B | 450 | 136,000 |
| BAR-C | 650 | 242,700 |

TABLE 13C

The results show count stability between an initial count and a one minute count, comparing BAR A and BAR C. LUMINATOR-T used with background subtract.

| | 60 fmoles ATP | |
|---|---|---|
|  | Initial Count | Count after 1 min. |
| BAR-A | 30,581 | 17,049 |
| BAR-C | 252,365 | 240,069 |

TABLE 13D

The results show count stability between an initial count and a one minute count, comparing BAR A and BAR C in testing a 10 microliter sample of raw milk pipetted onto a swab and then the swab is contacted with the BAR solution. LUMINATOR-T used with background subtract.

|  | Initial count | Count after 1 min. |
|---|---|---|
| BAR-A | 115,459 | 223,941 |
| BAR-C | 501,329 | 720,153 |

TABLE 13E

The results show temperature stability of BAR C in temperature stressed conditions versus standard conditions. LUMINATOR-K used with no background subtract.

|  | 0 count | 3.6 fmoles ATP |
|---|---|---|
| BAR-C | 661 | 14,644 |
| BAR-C (stressed) | 711 | 15,173 |

TABLE 13F

The results show increased sensitivity to 1.8 femtomoles ATP using BAR C as compared to BAR B and BAR A. LUMINATOR-T used with background subtract.

|  | Zero check | 1.8 fmoles ATP |
|---|---|---|
| BAR-A | 0, 0, 0, 0, 0 | 0, 0 |
| BAR-C | 0, 0, 0, 0, 0 | 3928/3236 |
| BAR-B | 0, 0, 0, 0, 0 | 828/567 |

What is claimed is:

1. A method for determining that a food contact surface has been sufficiently cleaned, after contact with an allergenic food, so that the surface does not contain at least 5 parts per million of the allergenic food, the method comprising:
   a) obtaining a sample from the surface;
   b) reacting said sample with reagents that generate luminescence in the presence of 0.05 femtomoles, or less, of ATP, said reagents comprising luciferin and luciferase;

c) exposing said sample, combined with said reagents, to a luminescence detector; and d) detecting the luminescence generated by the reaction of said sample with said reagents; and e) calculating the total amount of luminescence generated, by the reaction of said reagents with said sample, during a predetermined period of time, wherein the total luminescence generated, during the predetermined period of time, is used to determine whether the surface may contain at least 5 parts per million of the allergenic food.

2. The method of claim 1 wherein said predetermined period of time is less than about 60 seconds.

3. The method of claim 2 wherein the total luminescence generated, during the predetermined period of time of less than about 60 seconds, is multiplied by a predetermined factor and said result, multiplied by said predetermined factor, is used to predict the total luminescence that would be generated during a period of time longer than said predetermined period of time of less than 60 seconds, and wherein the predicted total luminescence is used to determine whether the surface has been sufficiently cleaned.

4. The method of claim 3 wherein a regression formula is used to predict total luminescence that would be generated over said longer period of time.

5. The method of claim 4 wherein said regression formula comprises a non-linear regression formula.

6. The method of claim 5 wherein said non-linear regression formula is selected from the group consisting of: a power curve formula; an exponential curve formula and a polynomial curve formula.

7. The method of claim 3 wherein an average of results from two or more different regression formulas is used to predict total luminescence that would be generated over an extended period of time.

8. The method of claim 1 wherein said predetermined period of time is about 20 seconds.

9. The method of claim 1 wherein said sample reacts with said reagents in a solution and wherein said solution comprises at least one buffer and wherein the total buffer concentration is less than about 10 millimolar.

10. The method of claim 9 wherein said at least one buffer comprises a phosphate buffer.

11. The method of claim 10 wherein said at least one buffer comprises a dibasic phosphate buffer.

12. The method of claim 9 wherein said solution further comprises a detergent.

13. The method of claim 12 wherein said detergent comprises benzalkonium chloride.

14. The method of claim 13 wherein the percentage of said benzalkonium chloride within said solution is less than about 0.01 percent.

15. The method of claim 14 wherein the percentage of said benzalkonium chloride within said solution is about 0.005 percent.

16. The method of claim 1 wherein the pH of the reagents is less than 7.2.

17. The method of claim 1 wherein the pH of the reagents is between 6.4 and 7.2.

18. The method of claim 1 wherein the allergenic food comprises peanut butter.

19. The method of claim 1 wherein the allergenic food comprises peanuts.

20. The method of claim 1 wherein the allergenic food comprises milk.

21. The method of claim 1 wherein the allergenic food comprises egg.

22. The method of claim 1 wherein said calculating comprises summing selected incremental luminescent counts during said predetermined period of time.

23. The method of claim 22 wherein said selected incremental counts comprises one second counts.

24. The method of claim 1 wherein said surface sample comprises rinse water from the surface.

\* \* \* \* \*